(12) United States Patent
Eichhorn et al.

(10) Patent No.: US 9,062,208 B2
(45) Date of Patent: Jun. 23, 2015

(54) FIBER-REACTIVE COPPER COMPLEX DISAZO DYES

(75) Inventors: Joachim Eichhorn, Frankfurt (DE); Andreas Schrell, Hofheim (DE)

(73) Assignee: DyStar Colours Distribution GmbH (DE)

(*) Notice: Subject to any disclaimer, the term of this patent is extended or adjusted under 35 U.S.C. 154(b) by 87 days.

(21) Appl. No.: 13/146,341

(22) PCT Filed: Jan. 18, 2010

(86) PCT No.: PCT/EP2010/050495
§ 371 (c)(1),
(2), (4) Date: Jul. 26, 2011

(87) PCT Pub. No.: WO2010/086243
PCT Pub. Date: Aug. 5, 2010

(65) Prior Publication Data
US 2011/0283465 A1    Nov. 24, 2011

(30) Foreign Application Priority Data
Jan. 27, 2009 (DE) .................. 10 2009 000 423

(51) Int. Cl.
| | |
|---|---|
| C09B 62/515 | (2006.01) |
| C09B 62/453 | (2006.01) |
| C09B 62/513 | (2006.01) |
| C07D 213/30 | (2006.01) |
| C09B 45/24 | (2006.01) |
| C09B 62/44 | (2006.01) |
| C09D 11/328 | (2014.01) |
| D06P 1/10 | (2006.01) |

(52) U.S. Cl.
CPC ............ *C09B 62/515* (2013.01); *C07D 213/30* (2013.01); *C09B 45/24* (2013.01); *C09B 62/4401* (2013.01); *D06P 1/10* (2013.01); *C09B 62/4416* (2013.01); *C09D 11/328* (2013.01)

(58) Field of Classification Search
USPC ..................................... 8/636, 549
See application file for complete search history.

(56) References Cited

U.S. PATENT DOCUMENTS

| | | | |
|---|---|---|---|
| 4,564,672 A | 1/1986 | Schlafer | |
| 6,521,032 B1* | 2/2003 | Lehmann et al. | 106/31.51 |
| 7,132,517 B2 | 11/2006 | Schwaiger et al. | |
| 2005/0241079 A1* | 11/2005 | Russ et al. | 8/643 |
| 2009/0041938 A1 | 2/2009 | Giehl | |

FOREIGN PATENT DOCUMENTS

| | | |
|---|---|---|
| CA | 2142742 A1 | 8/1995 |
| EP | 0144704 A2 | 6/1985 |
| EP | 0668328 A2 | 8/1995 |
| JP | 47036838 Y1 | 11/1972 |
| JP | 63-205368 A | 8/1988 |
| WO | WO-2007/085572 A2 | 8/2007 |

* cited by examiner

*Primary Examiner* — Harold Pyon
*Assistant Examiner* — Katie L Hammer
(74) *Attorney, Agent, or Firm* — Drinker Biddle & Reath LLP

(57) ABSTRACT

The present invention relates to dyes of the formula (I), in which $R^1$ to $R^4$, $D^1$, f, and M are defined as indicated in claim 1, to processes for preparing them, and to their use for dyeing and printing hydroxyl- and/or carboxamido-containing materials.

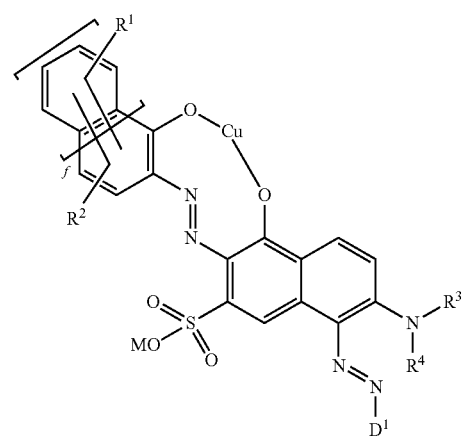

14 Claims, No Drawings

FIBER-REACTIVE COPPER COMPLEX DISAZO DYES

CROSS REFERENCE TO RELATED APPLICATIONS

This application is a national stage application (under 35 U.S.C. §371) of PCT/EP2010/050495, filed Jan. 18, 2010, which claims benefit of Germany application 10 2009 000 423.8, filed Jan. 27, 2009.

BACKGROUND OF THE INVENTION

The invention is situated within the technical field of fiber-reactive azo dyes.

Fiber-reactive azo dyes for dyeing hydroxyl- and carboxamido-containing materials in violet to blue hues are described in large number in the literature. The known dyes, however, often possess certain performance defects, such as, for example, inadequate light fastnesses or a deficient or unlevel buildup of color on cotton (good color buildup reflects the capacity of a dye when employed at increased dyebath concentrations to yield a stronger-colored dyeing to match), or a color yield which is too heavily dependent on fluctuating dyeing parameters in the dyeing operation. Possible consequences of these defects include, for example, poor reproducibilities on the part of the dyeings, which ultimately impacts the bottom line of the dyeing operation.

Consequently there continues to be a need for new reactive dyes having improved properties, such as high substantivity in combination with easy washoff of unfixed portions. They must also, furthermore, exhibit good dyeing yields and possess a high reactivity, the intention being more particularly to provide dyeings having high degrees of fixation.

BRIEF SUMMARY OF THE INVENTION

With the present invention, dyes have now been found which possess the above-described properties to a high degree.

The invention provides dyes of the formula (I)

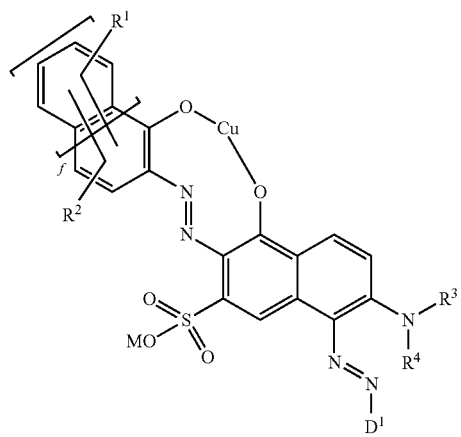

in which $R^1$ and $R^2$ independently of one another are hydrogen, $(C_1-C_4)$-alkyl, $(C_1-C_4)$-alkoxy, hydroxyl, sulfo, carboxyl, cyano, nitro, amido, ureido or halogen, or are a group of the formula $-SO_2-Z^1$, where $Z^1$ is $-CH=CH_2$, $-CH_2CH_2G$ or hydroxyl, and G is hydroxyl or an alkali-detachable group;

$R^3$ is $(C_1-C_4)$-alkyl; $(C_1-C_4)$-alkyl substituted by sulfo, carboxyl, halogen, hydroxyl, amino or acetamido; phenyl; or phenyl substituted by $(C_1-C_4)$-alkyl, $(C_1-C_4)$-alkoxy, sulfo, halogen, carboxyl, acetamido or ureido;

$R^4$ is hydrogen or has one of the definitions of $R^3$;

f is 0 or 1;

$D^1$ is a group of the formula (1)

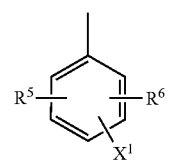

in which $R^5$ and $R^6$ independently of one another are hydrogen, $(C_1-C_4)$-alkyl, $(C_1-C_4)$-alkoxy, hydroxyl, sulfo, carboxyl, cyano, nitro, amido, ureido or halogen; and $X^1$ is hydrogen or a group of the formula $-SO_2-Z^2$, where $Z^2$ has one of the definitions of $Z^1$;

$D^1$ is a group of the formula (2)

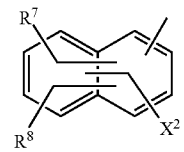

in which $R^7$ and $R^8$ independently of one another are hydrogen, $(C_1-C_4)$-alkyl, $(C_1-C_4)$-alkoxy, hydroxyl, sulfo, carboxyl, cyano, nitro, amido, ureido or halogen; and $X^2$ has one of the definitions of $X^1$; or $D^1$ is a group of the formula (3)

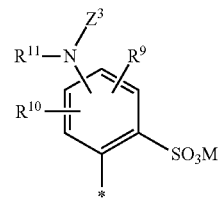

in which $R^9$ and $R^{10}$ independently of one another have one of the definitions of $R^5$ and $R^6$;

$R^{11}$ is hydrogen, $(C_1-C_4)$-alkyl, or phenyl which is unsubstituted or substituted by $(C_1-C_4)$-alkyl, $(C_1-C_4)$-alkoxy, sulfo, halogen or carboxyl; and $Z^3$ is a group of the formula (4) or (5) or (6)

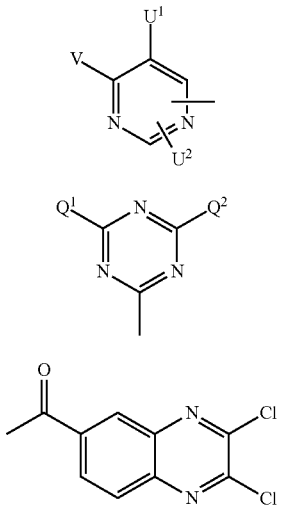

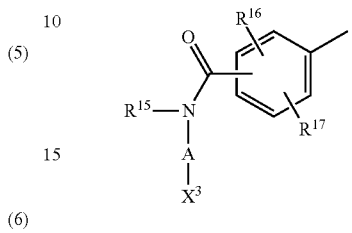

in which
V is fluorine or chlorine;
$U^1$ and $U^2$ independently of one another are fluorine, chlorine or hydrogen; and
$Q^1$ and $Q^2$ independently of one another are chlorine, fluorine, cyanamido, hydroxyl, $(C_1-C_6)$-alkoxy, phenoxy, sulfophenoxy, mercapto, $(C_1-C_4)$-alkylmercapto, pyridino, carboxypyridino or carbamoylpyridino, or are a group of the formula (7) or (8)

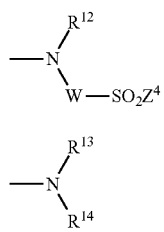

in which
$R^{12}$ is hydrogen, $(C_1-C_4)$-alkyl, sulfo-$(C_1-C_4)$-alkyl, unsubstituted phenyl or phenyl which is substituted by $(C_1-C_4)$-alkyl, $(C_1-C_4)$-alkoxy, sulfo, halogen, carboxyl, acetamido or ureido;
$R^{13}$ and $R^{14}$ independently of one another have one of the definitions of $R^{12}$ or together form a group of the formula —$(CH_2)_j$— where j is 4 or 5, or a group of the formula —$(CH_2)_2$-E-$(CH_2)_2$—, in which E is oxygen, sulfur, sulfonyl or —N(($C_1-C_4$)-alkyl)-;
W is unsubstituted phenylene; phenylene substituted by 1 or 2 substituents selected from the group consisting of $(C_1-C_4)$-alkyl, $(C_1-C_4)$-alkoxy, carboxyl, sulfo, chlorine, and bromine; unsubstituted naphthylene; naphthylene substituted by 1 or 2 sulfo groups; $(C_1-C_4)$-alkylene-arylene; $(C_1-C_4)$-alkylene-arylene which is interrupted by oxygen, sulfur, sulfonyl, —NH—, carbonyl, —CONH— or —CON(CH$_3$)—; $(C_2-C_6)$-alkylene; $(C_2-C_6)$-alkylene which is interrupted by oxygen, sulfur, sulfonyl, —NH—, carbonyl, —CONH— or —CON(CH$_3$)—; phenylene-CONH-phenylene; or phenylene-CONH -phenylene, where one or both phenylene groups are substituted each by 1 or 2 substituents selected from the group consisting of $(C_1-C_4)$-alkyl, $(C_1-C_4)$-alkoxy, hydroxyl, sulfo, carboxyl, amido, ureido, and halogen; and
$Z^4$ has one of the definitions of $Z^1$; or
$D^1$ is a group of the formula (9)

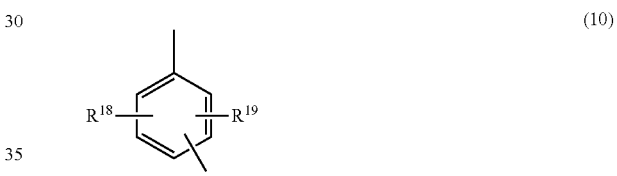

in which
$R^{15}$ is hydrogen, $(C_1-C_4)$-alkyl, aryl or an aryl substituted by one, two or three mutually independent groups from the series $(C_1-C_4)$-alkyl, $(C_1-C_4)$-alkoxy, hydroxyl, sulfo, carboxyl, amido, and halogen;
$R^{16}$ and $R^{17}$ independently of one another are hydrogen, $(C_1-C_4)$-alkyl, $(C_1-C_4)$-alkoxy, hydroxyl, sulfo, carboxyl, cyano, nitro, amido, ureido or halogen;
A is a group of the formula (10)

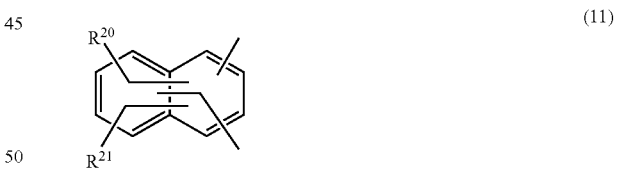

in which
$R^{18}$ and $R^{19}$ independently of one another are hydrogen, $(C_1-C_4)$-alkyl, $(C_1-C_4)$-alkoxy, hydroxyl, sulfo, carboxyl, cyano, nitro, amido, ureido or halogen; or
A is a group of the general formula (11)

(11)

in which
$R^{20}$ and $R^{21}$ independently of one another are hydrogen, $(C_1-C_4)$-alkyl, $(C_1-C_4)$-alkoxy, hydroxyl, sulfo, carboxyl, cyano, nitro, amido, ureido or halogen; or
A is a group of the formula (12)

 —$(CR^{22}R^{23})_k$— (12)

in which
k is an integer greater than 1 and
$R^{22}$ and $R^{23}$ independently of one another are hydrogen, $(C_1-C_4)$-alkyl, $(C_1-C_4)$-alkoxy, hydroxyl, cyano, amido, halogen or aryl; and
$X^3$ has one of the definitions of $X^1$; and
M is hydrogen, an alkali metal or one equivalent of an alkaline earth metal;

and the dyes of the formula (I) comprise at least one fiber-reactive group from the series —SO$_2$—Z$^1$, —SO$_2$—Z$^2$ and Z$^3$.

A DETAILED DESCRIPTION OF THE INVENTION (C$_1$-C$_4$)-alkyl groups may be straight-chain or branched and are more particularly methyl, ethyl, n-propyl, isopropyl, n-butyl, isobutyl, sec-butyl or tert-butyl. (C$_1$-C$_6$) groups may, furthermore, also be, for example, pentyl and hexyl. Preference is given to methyl and ethyl. Similar comments apply to alkoxy, alkylmercapto, and sulfoalkyl, and also to alkylene groups.

Aryl stands more particularly for phenyl, arylene for phenylene. Halogen is more particularly fluorine, chlorine or bromine, with fluorine and chlorine being preferred. M is preferably hydrogen, lithium, sodium or potassium, more preferably hydrogen or sodium.

Examples of alkali-detachable groups represented by G include halogen, such as chlorine and bromine; ester groups of organic carboxylic and sulfonic acids, such as alkylcarboxylic acids, unsubstituted or substituted benzenecarboxylic acids, and unsubstituted or substituted benzenesulfonic acids, such as the groups (C$_2$-C$_5$)-alkanoyloxy, including more particularly acetyloxy, benzoyloxy, sulfobenzoyloxy, phenylsulfonyloxy, and tolylsulfonyloxy; acidic ester groups of inorganic acids, such as of phosphoric acid, sulfuric acid, and thiosulfuric acid (phosphato, sulfato, and thiosulfato groups), or di-(C$_1$-C$_4$)-alkylamino groups, such as dimethylamino and diethylamino.

Z$^1$, Z$^2$ and Z$^4$ are preferably vinyl or β-chloroethyl and more preferably β-sulfatoethyl.

The groups "sulfo", "carboxyl", "thiosulfato", "phosphato", and "sulfato" include not only their acid form but also their salt form. Accordingly, sulfo groups have the formula —SO$_3$M, thiosulfato groups have the formula —S—SO$_3$M, carboxyl groups have the formula —COOM, phosphato groups have the formula —OPO$_3$M$_2$, and sulfato groups have the formula —OSO$_3$M, in each of which M is defined as indicated above.

The dyes of the formula (I) may possess different fiber-reactive groups —SO$_2$—Z$^1$ within the meaning of Z$^1$. In particular, —SO$_2$—Z$^1$ may in one case be vinylsulfonyl and in the other —CH$_2$CH$_2$G, preferably β-sulfatoethyl-sulfonyl. Where the dyes of the formula (I) partly contain vinylsulfonyl groups, the fraction of the respective dye with the vinylsulfonyl group is up to about 80 mol %, based on the respective total dye amount.

Similar comments apply to the groups —SO$_2$—Z$^2$ and —SO$_2$—Z$^4$.

The radicals R$^1$ and R$^2$ are preferably, independently of one another, hydrogen, (C$_1$-C$_4$)-alkyl, (C$_1$-C$_4$)-alkoxy, sulfo, carboxyl or a group of the formula —SO$_2$Z$^1$, and more preferably hydrogen, methyl, methoxy, sulfo or a group of the formula —SO$_2$Z$^1$, in which Z$^1$ more particularly is vinyl or β-sulfatoethyl.

R$^3$ is preferably methyl or sulfomethyl, with methyl being particularly preferred. R$^4$ is preferably hydrogen or methyl, with hydrogen being particularly preferred.

R$^5$ and R$^6$ are preferably, independently of one another, hydrogen, (C$_1$-C$_4$)-alkyl, (C$_1$-C$_4$)-alkoxy, sulfo or carboxyl, and more preferably hydrogen, methyl, methoxy or sulfo.

R$^7$ to R$^{10}$, R$^{20}$, and R$^{21}$ are preferably, independently of one another, hydrogen or sulfo.

R$^{16}$ to R$^{19}$, R$^{22}$, and R$^{23}$ are preferably hydrogen.

R$^{11}$, R$^{12}$, and R$^{15}$ are preferably, independently of one another, hydrogen, methyl or phenyl.

R$^{13}$ and R$^{14}$ are preferably, independently of one another, hydrogen, methyl, 2-sulfoethyl, 2-, 3- or 4-sulfophenyl, or together they form the group —(CH$_2$)$_2$—O—(CH$_2$)$_2$—.

D$^1$ is preferably a group of the formula (1) or a group of the formula (3) or (9), in which, more particularly, R$^9$ to R$^{11}$ and R$^{15}$ to R$^{17}$, respectively, possess the preferred definitions described above.

Where D$^1$ is a group of the formula (1) and X$^1$ is —SO$_2$Z$^2$, —SO$_2$—Z$^2$ is preferably positioned meta or para to the diazo group.

Preferred groups of the formula (1) are, for example, 2-, 3- or 4-sulfophenyl, 2-, 3- or 4-carboxyphenyl, 2,4-disulfophenyl, 2,5-disulfophenyl, 4-carboxy-2-sulfo-phenyl, 5-carboxy-2-sulfo-phenyl, 4-methyl-2-sulfo-phenyl, 4-methoxy-2-sulfo-phenyl, 5-methoxy-2-sulfo-phenyl, 2-methoxy-5-methyl-4-sulfo-phenyl, 2,5-dimethoxy-4-sulfo-phenyl, 1-sulfo-naphth-2-yl, 1,5-disulfo-naphth-2-yl, 4,8-disulfo-naphth-2-yl, 2(β-sulfatoethylsulfonyl)-phenyl, 3-(β-sulfatoethylsulfonyl)-phenyl, 4-(β-sulfatoethylsulfonyl)-phenyl, 2-carboxy-5-(β-sulfatoethylsulfonyl)-phenyl, 2-chloro-4-(β-sulfatoethylsulfonyl)-phenyl, 2-chloro-5-(β-sulfatoethylsulfonyl)-phenyl, 2-bromo-4-(β-sulfatoethylsulfonyl)-phenyl, 2-sulfo-4-(β-sulfatoethylsulfonyl)-phenyl, 2-sulfo-5-(β-sulfatoethylsulfonyl)-phenyl, 2-methoxy-5-(β-sulfatoethylsulfonyl)-phenyl, 2-ethoxy-5-(β-sulfatoethylsulfonyl)-phenyl, 2,5-dimethoxy-4-(β-sulfatoethylsulfonyl)-phenyl, 2-methoxy-5-methyl-4-(β-sulfatoethylsulfonyl)-phenyl, 2-methyl-4-(β-sulfatoethylsulfonyl)-phenyl, 2- or 3- or 4-(β-thiosulfatoethylsulfonyl)-phenyl, 2-methoxy-5-(β-thiosulfatoethylsulfonyl)-phenyl, 2-sulfo-4-(β-phosphatoethylsulfonyl)-phenyl, 2- or 3- or 4-vinylsulfonyl-phenyl, 2-sulfo-4-vinylsulfonyl-phenyl, 2-chloro-4-(β-chloroethylsulfonyl)-phenyl, 2-chloro-5-(β-chloroethylsulfonyl)-phenyl, 3- or 4-(β-acetoxyethylsulfonyl)-phenyl, 6- or 8-(β-sulfatoethylsulfonyl)-naphth-2-yl, 6-(β-sulfatoethylsulfonyl)-1-sulfo-naphth-2-yl, and 8-(β-sulfatoethylsulfonyl)-6-sulfo-naphth-2-yl, including preferably 3-(β-sulfatoethylsulfonyl)-phenyl, 4-(β-sulfatoethylsulfonyl)-phenyl, 2-sulfo-4-(β-sulfatoethylsulfonyl)-phenyl, 2-methoxy-5-(β-sulfatoethylsulfonyl)-phenyl, 2,5-dimethoxy-4-(β-sulfatoethylsulfonyl)-phenyl, 2-methoxy-5-methyl-4-(β-sulfatoethylsulfonyl)-phenyl, and 3- or 4-vinylsulfonyl-phenyl.

Where D$^1$ is a group of the formula (2), the bond to the diazo group is preferably positioned β to the naphthalene nucleus.

Where D$^1$ is a group of the formula (9), the group —CON(R$^{15}$)-A-X$^3$ is preferably positioned para or meta to the diazo group.

Where A is a group of the formula (10) and X$^3$ is a group of the formula —SO$_2$—Z$^2$, the —SO$_2$—Z$^2$ group is preferably positioned meta or para to the nitrogen atom.

Where A is a group of the formula (11), the bond to the nitrogen atom is preferably positioned β to the naphthalene nucleus.

Examples of substituents represented by A are, in particular, 1,2-phenylene, 1,3-phenylene, 1,4-phenylene, 2-chloro-1,4-phenylene, 2-chloro-1,5-phenylene, 2-bromo-1,4-phenylene, 2-sulfo-1,4-phenylene, 2-sulfo-1,5-phenylene, 2-methoxy-1,5-phenylene, 2-ethoxy-1,5-phenylene, 2,5-dimethoxy-1,4-phenylene, 2-methoxy-5-methyl-1,4-phenylene, 2-methyl-1,4-phenylene, 2,6-naphthylene, 2,8-naphthylene, 1-sulfo-2,6-naphthylene, 6-sulfo-2,8-naphthylene, 1,2-ethylene, and 1,3-propylene. More preferably A is 1,3-phenylene, 1,4-phenylene, 2-sulfo-1,4-phenylene, 2-methoxy-1,5-phenylene, 2,5-dimethoxy-1,4-phenylene, 2-methoxy-5-methyl-1,4-phenylene, 1,2-ethylene or 1,3-propylene, and, in the case of 1,2-ethylene and 1,3-propylene, $R^{15}$ is preferably phenyl and 2-sulfophenyl.

k is preferably the number 2 or 3.

W is preferably 1,3-phenylene, 1,4-phenylene, 2-sulfo-1,4-phenylene, 2-methoxy-1,5-phenylene, 2,5-dimethoxy-1,4-phenylene, 2-methoxy-5-methyl-1,4-phenylene, 1,2-ethylene or 1,3-propylene.

Examples of the groups $Q^1$ and $Q^2$ are fluorine, chlorine, hydroxyl, methoxy, ethoxy, phenoxy, 3-sulfophenoxy, 4-sulfophenoxy, methyl mercapto, cyanamido, amino, methylamino, ethylamino, morpholino, piperidino, phenylamino, methylphenylamino, 2-sulfophenylamino, 3-sulfophenylamino, 4-sulfophenyl-amino, 2,4-disulfophenylamino, 2,5-disulfophenylamino, 2-sulfoethylamino, N-methyl-2-sulfoethylamino, pyridino, 3-carboxypyridino, 4-carboxypyridino, 3-carbamoylpyridino, 4-carbamoylpyridino, 2-(2-sulfatoethylsulfonyl)-phenylamino, 3-(2-sulfatoethylsulfonyl)-phenylamino, 4-(2-sulfatoethylsulfonyl)-phenylamino, N-ethyl-3-(2-sulfatoethylsulfonyl)-phenylamino, N-ethyl-4-(2-sulfatoethylsulfonyl)-phenylamino, 2-carboxy-5-(2-sulfatoethylsulfonyl)-phenylamino), 2-chloro-4-(2-sulfatoethylsulfonyl)-phenylamino, 2-chloro-5-(2-sulfatoethylsulfonyl)-phenylamino, 2-bromo-4-(2-sulfatoethylsulfonyl)-phenylamino, 2-sulfo-4-(2-sulfatoethylsulfonyl)-phenylamino, 2-sulfo-5-(2-sulfatoethylsulfonyl)-phenylamino, 2-methoxy-5-(2-sulfatoethylsulfonyl)-phenylamino, 2,5-dimethoxy-4-(2-sulfatoethylsulfonyl)-phenylamino, 2-methoxy-5-methyl-4-(2-sulfatoethylsulfonyl)-phenylamino, 2-methyl-4-(2-sulfatoethylsulfonyl)-phenylamino, 2-(vinylsulfonyl)-phenylamino, 3-(vinylsulfonyl)-phenylamino, 4-(vinylsulfonyl)-phenylamino), N-ethyl-3-(vinylsulfonyl)-phenylamino, N-ethyl-4-(vinylsulfonyl)-phenylamino, 6-(2-sulfatoethylsulfonyl)-naphth-2-ylamino, 8-(2-sulfatoethylsulfonyl)-naphth-2-ylamino, 8-(2-sulfatoethylsulfonyl)-6-sulfo-naphth-2-ylamino, 3-(2-(2-sulfatoethylsulfonyl)-ethylcarbamoyl)-phenylamino, 4-(2-(2-sulfatoethylsulfonyl)-ethylcarbamoyl)-phenylamino, 3-(2-(vinylsulfonyl)-ethylcarbamoyl)-phenylamino, 4-(2-(2-vinylsulfonyl)-ethylcarbamoyl)-phenylamino, 4-(N-methyl-2-(2-sulfatoethylsulfonyl)-ethylcarbamoyl)-phenylamino, 4-(N-phenyl-2-(2-sulfatoethylsulfonyl)-ethylcarbamoyl)-phenylamino, 4-(3-(2-sulfatoethylsulfonyl)-phenylcarbamoyl)-phenylamino, 4-(4-(2-sulfatoethylsulfonyl)-phenylcarbamoyl)-phenylamino, 3-(3-(2-sulfatoethylsulfonyl)-phenylcarbamoyl)-phenylamino, 3-(4-(2-sulfatoethylsulfonyl)-phenylcarbamoyl)-phenylamino, 3-(2-sulfatoethylsulfonyl)-propylamino, N-methyl-N-(2-(2-sulfatoethylsulfonyl)-ethyl)-amino, N-phenyl-N-(2-(2-sulfatoethylsulfonyl)-ethyl)-amino, and N-phenyl-N-(2-(2-sulfatoethylsulfonyl)-propyl)-amino.

Preferably the groups $Q^1$ and $Q^2$ independently of one another are fluorine, chlorine, cyanamido, morpholino, 2-sulfophenylamino, 3-sulfophenylamino, 4-sulfophenylamino, N-methyl-2-sulfoethylamino, 3-carboxypyridino, 4-carboxy-pyridino, 3-carbamoylpyridino, 4-carbamoylpyridino, 3-(2-sulfatoethylsulfonyl)-phenylamino, 4-(2-sulfatoethylsulfonyl)-phenylamino, 3-(vinylsulfonyl)-phenylamino, 4-(vinylsulfonyl)-phenylamino), 4-(3-(2-sulfatoethylsulfonyl)-phenylcarbamoyl)-phenylamino, 4-(4-(2-sulfatoethylsulfonyl)-phenylcarbannoyl)-phenylamino, 3-(3-(2-sulfatoethylsulfonyl)-phenylcarbamoyl)-phenylamino, 3-(4-(2-sulfatoethylsulfonyl)-phenylcarbamoyl)-phenylamino, N-methyl-N-(2-(2-sulfatoethylsulfonyl)-ethyl)-amino or N-phenyl-N-(2-(2-sulfatoethylsulfonyl)-ethyl)-amino.

More preferably the groups $Q^1$ and $Q^2$ independently of one another are fluorine, chlorine, cyanamido, morpholino, 2-sulfophenylamino, 3-sulfophenylamino, 4-sulfophenylamino, 3-(2-sulfatoethylsulfonyl)-phenylamino, 4-(2-sulfatoethylsulfonyl)-phenylamino, 3-(vinylsulfonyl)-phenylamino, 4-(vinylsulfonyl)-phenylamino), N-methyl-N-(2-(2-sulfatoethylsulfonyl)-ethyl)-amino or N-phenyl-N-(2-(2-sulfatoethylsulfonyl)-ethyl)-amino.

Examples of $Z^3$ are 2,4-difluoro-pyrimidin-6-yl, 4,6-difluoro-pyrimidin-2-yl, 5-chloro-2,4-difluoro-pyrimidin-6-yl, 5-chloro-4,6-difluoro-pyrimidin-2-yl, 4,5-difluoro-pyrimidin-6-yl, 5-chloro-4-fluoro-pyrimidin-6-yl, 2,4,5-trichloro-pyrimidin-6-yl, 4,5-dichloro-pyrimidin-6-yl, 2,4-dichloro-pyrimidin-6-yl, 4-fluoro-pyrimidin-6-yl, 4-chloro-pyrimidin-6-yl, the group of the formula (5) with the above-indicated examples for $Q^1$ and $Q^2$, and the group of the formula (6).

Preferably $Z^3$ is 2,4-difluoro-pyrimidin-6-yl, 4,6-difluoro-pyrimidin-2-yl, 5-chloro-2,4-difluoro-pyrimidin-6-yl, 5-chloro-4,6-difluoro-pyrimidin-2-yl or a group of the general formula (5) with the above-indicated preferred groups $Q^1$ and $Q^2$.

More preferably $Z^3$ is 2,4-difluoro-pyrimidin-6-yl, 5-chloro-2,4-difluoro-pyrimidin-6-yl or a group of the general formula (5) with the above-indicated more-preferred groups $Q^1$ and $Q^2$.

Preferred dyes conform to the formula (Ia)

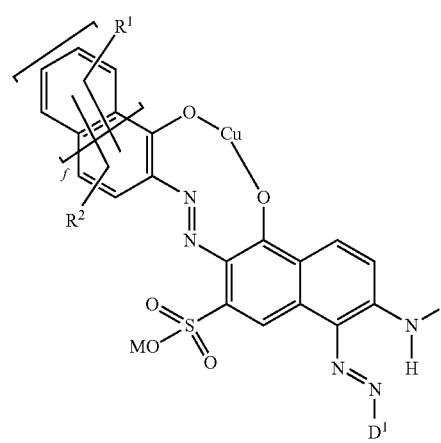

(Ia)

in which $R^1$ to $R^3$, $D^1$, f, and M are defined as indicated above.

Particularly preferred dyes conform to the formula (Ib)

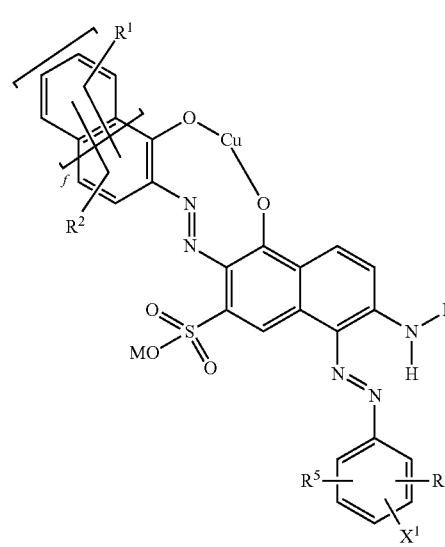

(Ib)

in which $R^1$ to $R^3$, $R^5$, $R^6$, $X^1$, f, and M are defined as indicated above.

Especially preferred dyes conform to the formula (Ic)

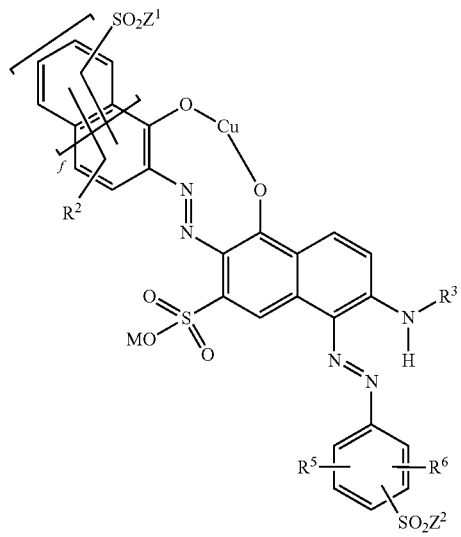

in which $R^2$, $R^5$, $R^6$, $Z^1$, $Z^2$, f, and M are defined as indicated above.

Dyes of the invention in which f is 0 conform to the formula (Id)

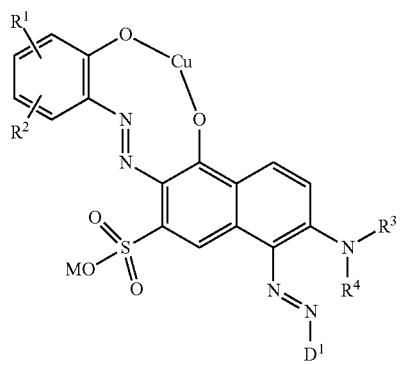

in which $R^1$ to $R^4$, $D^1$, and M are defined as indicated above.

Dyes of the invention in which f is 1 conform to the formula (Ie)

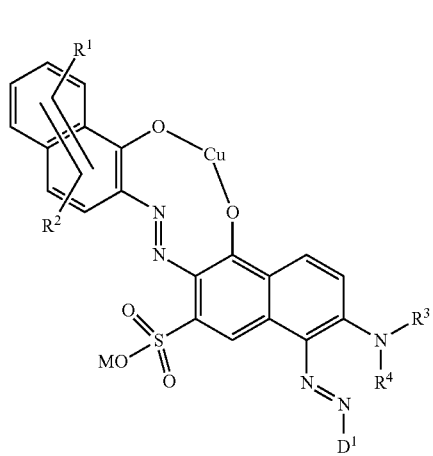

in which $R^1$ to $R^4$, $D^1$, and M are defined as indicated above.

The dyes of the formula (I) according to the invention may be present as a preparation in solid or in liquid (dissolved) form. In solid form they comprise, to the extent necessary, the electrolyte salts which are customary for water-soluble and, in particular, fiber-reactive dyes, such as sodium chloride, potassium chloride, and sodium sulfate, and may further comprise the auxiliaries that are customary in commercial dyes, such as buffer substances capable of setting a pH of between 3 and 7 in aqueous solution, such as sodium acetate, sodium citrate, sodium borate, sodium hydrogencarbonate, sodium dihydrogenphosphate, and disodium hydrogenphosphate, and additionally dyeing auxiliaries, antidust agents, and small amounts of siccatives. If they are present in liquid, aqueous solution (including the content of thickeners of the kind customary for print pastes), they may also comprise substances which ensure a long life for these preparations, such as mold preventatives, for example.

In solid form, the dyes of the formula (I) according to the invention are typically in the form of powders or granules which contain electrolyte salts (referred to generally, below, as preparations) with, where appropriate, one or more of the abovementioned auxiliaries. In the preparations the dyes are present at 20% to 90% by weight, based on the preparation. The buffer substances are generally present in a total amount of up to 5% by weight, based on the preparation.

Where the dyes of the formula (I) according to the invention are present in aqueous solution, the total dye content of these aqueous solutions is up to about 50% by weight, such as, for example, between 5% and 50% by weight, the electrolyte salt content of these aqueous solutions being preferably below 10% by weight, based on the aqueous solution; the aqueous solutions (liquid preparations) may contain the aforementioned buffer substances in general in an amount of up to 5% by weight, preferably up to 2% by weight.

The dyes of the general formula (I) according to the invention can be prepared in analogy to customary procedures known to the person skilled in the art. More particularly a compound of the formula (13)

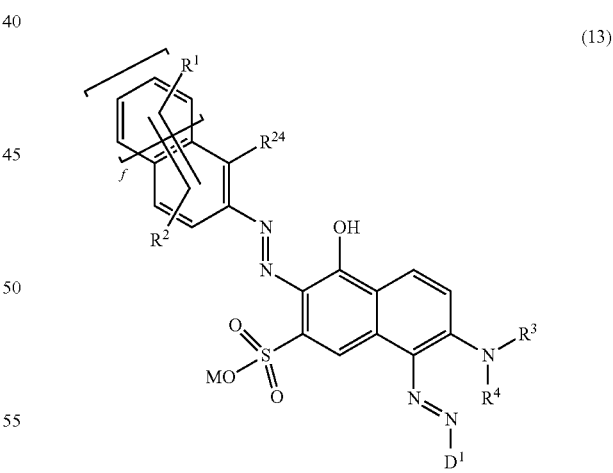

in which $R^{24}$ is hydrogen, hydroxyl or methoxy and $R^1$ to $R^4$, $D^1$, and M are defined as indicated above is reacted with a copper(II) salt.

A suitable copper(II) salt is, in particular, copper(II) sulfate. The reaction takes place if necessary at relatively high temperatures and preferably with the use of equimolar amounts of the copper(II) salt. If $R^{24}$ is hydrogen, the reaction takes place sensibly in the presence of an oxidizing agent, more particularly of hydrogen peroxide.

The compound of the formula (13) is obtained, for example, by
a) diazotizing an amine of the formula (14)

in which $D^1$ is defined as indicated above,
b) subsequently reacting the resulting diazonium compound with a compound of the formula (15)

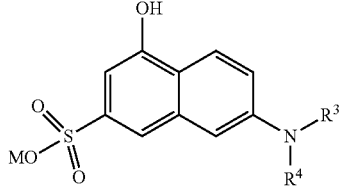

in which $R^3$, $R^4$, and M are defined as indicated above, to give a compound of the formula (16)

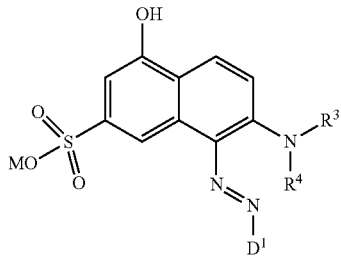

in which $D^1$, $R^3$, $R^4$, and M are defined as indicated above, subsequently
c) diazotizing a compound of the general formula (17)

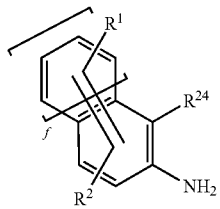

in which $R^1$, $R^2$, and f are defined as indicated above and $R^{24}$ is hydrogen, hydroxyl or methoxy, and
d) carrying out reaction with the compound of the formula (16) to give the compound of the formula (13).

In an alternative process the dye of the formula (I) is prepared by reacting a compound of the formula (18)

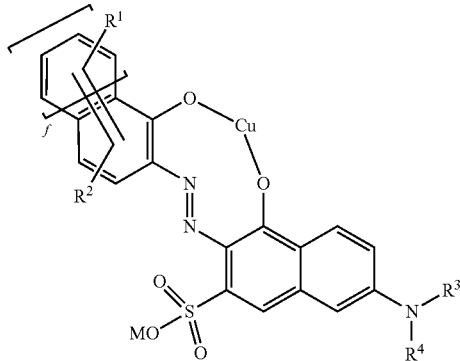

in which $R^1$ to $R^4$, f, and M are defined as indicated above, with the diazotized compound of an amine of the formula (14).

The compound of the formula (18) can be obtained by diazotizing a compound of the formula (17) in which $R^1$, $R^2$, $R^{24}$, and f are defined as indicated above, and carrying out reaction with a compound of the formula (15) in which $R^3$, $R^4$, and M are defined as indicated above at pH levels above 6 in a first stage, and subsequently carrying out reaction, as described above, with a copper(II) salt.

The diazotization, coupling, and coppering reactions described are known to the person skilled in the art and are described comprehensively in the literature.

Dyes which as well as —$CH_2CH_2G$ groups also have vinylsulfonyl groups as reactive radicals can be prepared not only starting from correspondingly substituted vinylsulfonyl compounds but also by reaction of corresponding dyes containing —$CH_2CH_2G$ groups with alkali in an amount which converts the desired proportion of —$CH_2CH_2G$ groups into vinylsulfonyl groups. This conversion takes place in a way with which the person skilled in the art is familiar. In some cases vinylsulfonyl groups are formed even during the dye synthesis.

The dyes of the formula (I) according to the invention can be isolated in conventional manner by being salted out, using common salt or potassium chloride, for example, or by spray drying or evaporation. An alternative option is to put the as-synthesized solutions, where necessary following addition of a buffer substance and if desired after concentration, to dyeing use directly, in the form of liquid preparations.

The dyes of the general formula (I) according to the invention possess valuable performance properties and can be used for dyeing and printing carboxamido- and/or hydroxyl-containing materials. The stated materials may take the form, for example, of sheetlike structures such as paper and leather, the form of films, such as polyamide films, for example, or the form of a bulk composition, as of polyamide or polyurethane, for example. More particularly, however, they take the form of fibers of the stated materials.

Thus the dyes of the general formula (I) according to the invention are used for dyeing and printing cellulosic fiber materials of all kinds. They are preferably also suitable for dyeing or printing polyamide fibers or blend fabrics of polyamide with cotton or with polyester fibers.

It is also possible to use the dyes of the general formula (I) according to the invention to print textiles or paper by the inkjet process.

The present invention accordingly also provides for the use of the dyes of the general formula (I) according to the invention for dyeing or printing carboxamido- and/or hydroxyl-containing materials, and processes for dyeing or printing such materials in conventional procedures, by using one or more dyes of the general formula (I) according to the invention as colorants.

Fibers or fiber materials for the purposes of the present invention are more particularly textile fibers, which may be present as woven fabrics or as yarns or in the form of hanks or wound packages.

Carboxamido-containing materials are, for example, synthetic and natural polyamides and polyurethanes, more particularly in the form of fibers, examples being wool and other animal hairs, silk, leather, nylon-6,6, nylon-6, nylon-11, and nylon-4.

Hydroxyl-containing materials are those of natural or synthetic origin, such as, for example, cellulose fiber materials or their regenerated products and polyvinyl alcohols. Cellulose fiber materials are preferably cotton, but also other plant fibers, such as linen, hemp, jute, and ramie fibers. Regenerated cellulose fibers are, for example, staple viscose and filament viscose.

The dyes of the general formula (I) according to the invention can be applied to and fixed on the stated materials, more particularly the stated fiber materials, by the application techniques that are known for water-soluble dyes, and particularly for fiber-reactive dyes.

Wool which has been given a nonfelting or low-felting finish (cf., for example, H. Rath, Lehrbuch der Textilchemie, Springer-Verlag, 3rd edition (1972), pp. 295-299, especially wool finished by the Hercosett process (p. 298); J. Soc. Dyers and Colourists 1972, 93-99, and 1975, 33-44) can be dyed with very good fastness properties. The process of dyeing on wool takes place here in a conventional dyeing procedure from an acidic medium. For example, acetic acid and/or ammonium sulfate or acetic acid and ammonium acetate or sodium acetate can be added to the dyebath in order to obtain the desired pH. To achieve a useful levelness in the dyeing, it is advisable to add customary leveling assistants, such as, for example, a leveling assistant based on a reaction product of cyanuric chloride with three times the molar amount of aminobenzenesulfonic acid and/or of an aminonaphthalenesulfonic acid, or one based on a reaction product of, for example, stearylamine with ethylene oxide. Thus, for example, the dye mixture of the invention is preferably first subjected to the exhaust process from an acidic dyebath having a pH of about 3.5 to 5.5, with monitoring of the pH, and then, toward the end of the dyeing time, the pH is shifted into the neutral and optionally weakly alkaline range, to a pH of up to 8.5, in order, in particular, to induce the full reactive binding between the dyes of the dye mixtures of the invention and the fiber, in order to obtain high depths of color. At the same time the fraction of dye which has not been reactively bound is removed.

The procedure described here also applies to the production of dyeings on fiber materials composed of other natural polyamides or of synthetic polyamides and polyurethanes. These materials can be dyed using the customary dyeing and printing processes that are described in the literature and known to the person skilled in the art (see, for example, H.-K. Rouette, Handbuch der Textilveredlung, Deutscher Fachverlag GmbH, Frankfurt am Main).

Besides the dyes of the general formulae (I) and water, the dyeing liquors and print pastes may comprise further additives. Additives are, for example, wetting agents, antifoams, leveling agents, and agents that influence the properties of the textile material, such as softeners, flame retardant finish additives, and agents which impart dirt, water, and oil repellency or that soften water. Print pastes in particular may also comprise natural or synthetic thickeners, such as alginates and cellulose ethers, for example. In the dyebaths and print pastes, the amounts of dye may vary within wide limits, in accordance with the desired depth of color. Generally speaking, the dyes of the general formula (I) are present in amounts of 0.01% to 15% by weight, more particularly in amounts of 0.1% to 10% by weight, based on the dyeing goods or the print paste, respectively.

On cellulose fibers, dyeings having very good color yields are obtained by the exhaust processes from a long liquor, using a wide variety of acid-binding agents and, where appropriate, neutral salts, such as sodium chloride or sodium sulfate. In the case of the exhaust process it is preferred to carry out dyeing at a pH of 3 to 7, more particularly at a pH of 4 to 6. The liquor ratio may be selected with a wide range and is for example between 3:1 and 50:1, preferably between 5:1 and 30:1. Dyeing is done preferably in an aqueous bath at temperatures between 40 and 105° C., optionally at a temperature up to 130° C. under superatmospheric pressure, and where appropriate in the presence of customary dyeing auxiliaries. The wet fastness properties of the dyed material can be enhanced by an aftertreatment to remove unfixed dye. This aftertreatment takes place more particularly at a pH of 8 to 9 and at temperatures of 75 to 80° C.

One possible exhaust process procedure is to introduce the material into the warm bath and to gradually heat the bath to the desired temperature and complete the dyeing operation. The neutral salts which accelerate the exhaustion of the dyes can also, if desired, not be added to the bath until the actual dyeing temperature has been reached.

The padding process on cellulose fibers likewise produces excellent color yields and a very good color buildup, with fixing able to take place in conventional manner by batching at room temperature or elevated temperature, at up to about 60° C., for example, by steaming or by means of dry heat.

The customary printing processes for cellulose fibers as well, which can be carried out in one step—as for example by printing with a print paste comprising sodium bicarbonate or another acid-binding agent and by subsequent steaming at 100 to 103° C.—or in two steps—as for example by printing with a neutral or weakly acidic printing ink, followed by fixing either by passage of the printed materials through a hot, electrolyte-containing alkaline bath or by overpadding with an alkaline, electrolyte-containing padding liquor, and subsequent batching or steaming or dry heat treatment of the alkali-overpadded material—produces strongly colored prints with well-defined contours and a clear white ground. The outcome of the prints is affected little, if at all, by variations in the fixing conditions.

In the case of fixing by means of dry heat, in accordance with the customary thermofix processes, hot air at 120 to 200° C. is used. Besides the customary steam at 101 to 103° C., it is also possible to use superheated steam and high-pressure steam at temperatures of up to 160° C.

The acid-binding agents which effect the fixation of the dyes on the cellulose fibers are, for example, water-soluble basic salts of the alkali metals and likewise alkaline earth metals of organic or inorganic acids or compounds which liberate alkali in the heat. Particularly included are the alkali metal hydroxides and alkali metal salts of weak to moderately strong organic or inorganic acids, the preferred alkali metal compounds being the sodium compounds and potassium compounds. Examples of such acid-binding agents include sodium hydroxide, potassium hydroxide, sodium carbonate, sodium bicarbonate, potassium carbonate, sodium formate, sodium dihydrogenphosphate, disodium hydrogenphosphate, sodium trichloroacetate, waterglass or trisodium phosphate, or mixtures thereof.

The dyes of the formula (I) according to the invention are notable in particular for high color strengths and fixing yields and ease of washoff of the portions not fixed on the fiber. Moreover, the dyeings and prints have good all-round fastness properties, such as high light fastness and very good wet fastnesses, such as fastness to washing, to water, to salt water, to cross-dyeing, and to perspiration, for example, and also good fastness to pleating, hot pressing, and rubbing. They exhibit, furthermore, little tendency to stain polyamide in cotton/polyamide blend fabrics. All in all, therefore, they have an improved profile of properties relative to the dyes known from JP 47036838.

The present invention also provides inks for digital textile printing by the inkjet process, which comprise a dye of the general formula (I) according to the invention. The inks of the invention comprise one or more of the dyes of the formula (I) according to the invention, in amounts, for example, of 0.1% to 50% by weight, preferably in amounts of 1% to 30% by weight, and more preferably in amounts of 1% to 15% by weight, based on the total weight of the ink. It will be appreciated that the inks may also comprise mixtures of dyes of the general formula (I) according to the invention and other dyes used in textile printing.

For the use of the inks in the continuous flow process, a conductivity of 0.5 to 25 mS/m can be set by addition of electrolyte. Examples of suitable electrolyte include lithium nitrate and potassium nitrate.

The inks of the invention may contain organic solvents with a total content of 1-50%, preferably of 5-30% by weight.

Examples of suitable organic solvents include alcohols, such as methanol, ethanol, 1-propanol, isopropanol, 1-butanol, tert-butanol, pentyl alcohol, polyhydric alcohols, such as 1,2-ethanediol, 1,2,3-propanetriol, butanediol, 1,3-butanediol, 1,4-butanediol, 1,2-propanediol, 1,3-propanediol, pentanediol, 1,4-pentanediol, 1,5-pentanediol, hexanediol, D,L-1,2-hexanediol, 1,6-hexanediol, 1,2,6-hexanetriol, 1,2-octanediol, polyalkylene glycols, such as polyethylene glycol, polypropylene glycol, alkylene glycols having 2 to 8 alkylene groups, e.g.: monoethylene glycol, diethylene glycol, triethylene glycol, tetraethylene glycol, thioglycol, thiodiglycol, butyltriglycol, hexylene glycol, propylene glycol, dipropylene glycol, tripropylene glycol, lower alkyl ethers of polyhydric alcohols, such as ethylene glycol monomethyl ether, ethylene glycol monoethyl ether, ethylene glycol monobutyl ether, diethylene glycol monomethyl ether, diethylene glycol monoethyl ether, diethylene glycol monobutyl ether, diethylene glycol monohexyl ether, triethylene glycol monomethyl ether, triethylene glycol monobutyl ether, tripropylene glycol monomethyl ether, tetraethylene glycol monomethyl ether, tetraethylene glycol monobutyl ether, tetraethylene glycol dimethyl ether, propylene glycol monomethyl ether, propylene glycol monoethyl ether, propylene glycol monobutyl ether, tripropylene glycol isopropyl ether, polyalkylene glycol ethers, such as polyethylene glycol monomethyl ether, polypropylene glycol glycerol ether, polyethylene glycol tridecyl ether, and polyethylene glycol nonylphenyl ether, amines, such as methylamine, ethylamine, diethylamine, triethylamine, diethylamine, dimethylamine, trimethylamine, dibutylamine, diethanolamine, triethanolamine, ethylenediamine, urea derivatives, such as urea, thiourea, N-methylurea, N,N'-dimethylurea, ethyleneurea, and 1,1,3,3-tetramethylurea, amides, such as dimethylformamide, dimethylacetamide, acetamide, N-formylethanolamine, N-acetylethanolamine, ketones or keto alcohols, such as acetone, diacetone alcohol, cyclic ethers, such as tetrahydrofuran, dioxane, and also trimethylolethane, trimethylolpropane, 2-butoxyethanol, benzyl alcohol, gamma-butyrolactone, epsilon-caprolactam, and additionally sulfolane, methylsulfolane, 2,4-dimethylsulfolane, dimethyl sulfone, butadiene sulfone, dimethyl sulfoxide, dibutyl sulfoxide, N-cyclohexylpyrrolidone, N-methyl-2-pyrrolidone, N-ethylpyrrolidone, 2-pyrrolidone, 1-(2-hydroxyethyl)-2-pyrrolidone, 1-(3-hydroxypropyl)-2-pyrrolidone, 1,3-dimethyl-2-imidazolidinone, 1,3-dimethyl-2-imidazolinone, 1,3-bismethoxymethyl-imidazolidine, 2-(2-methoxyethoxy)ethanol, 2-(2-ethoxyethoxy)ethanol, 2-(2-butoxy-ethoxy)ethanol, 2-(2-propoxyethoxy)ethanol, 1,2-dimethoxypropane, trimethoxypropane, pyridine, piperidine, ethyl acetate, ethylenediaminetetraacetate, and ethyl pentyl ether.

The inks of the invention may further comprise the customary additives, such as, for example, viscosity moderators to set viscosities in the range from 1.5 to 40.0 mPas in a temperature range from 20 to 50° C. Preferred inks have a viscosity of 1.5 to 20 mPas, and particularly preferred inks have a viscosity of 1.5 to 15 mPas.

Suitable viscosity moderators are rheological additives, examples being the following: polyvinylcaprolactam, polyvinylpyrrolidone, and also their copolymers, polyetherpolyol, associative thickeners, polyurea, polyurethane, sodium alginates, modified galactomannans, polyetherurea, polyurethane, and nonionic cellulose ethers.

As further additives the inks of the invention may include surface-active substances for setting surface tensions of 20 to 65 mN/m, which are adapted if necessary as a function of the process used (thermo or piezoelectric technology).

Examples of suitable surface-active substances include the following: surfactants of all kinds, preferably nonionic surfactants, butyldiglycol, and 1,2-hexanediol.

The inks may further comprise customary additives, such as substances for inhibiting fungal and bacterial growth, for example, in amounts of 0.01% to 1% by weight, based on the total weight of the ink.

The inks of the invention may be prepared in conventional manner by mixing of the components in water.

The inks of the invention are suitable for use in inkjet printing processes for printing a very wide variety of pretreated materials, such as silk, leather, wool, polyamide fibers and polyurethanes, and more particularly cellulosic fiber materials of all kinds. The printing inks of the invention are also suitable for printing pretreated hydroxyl- and/or amino-containing fibers that are present in blend fabrics; for example, mixtures of cotton, silk, wool with polyester fibers or polyamide fibers.

In contrast to conventional textile printing, where the printing ink already contains all of the fixing chemicals and thickeners for a reactive dye, it is necessary in the case of inkjet printing to apply the auxiliaries to the textile substrate in a separate pretreatment step.

The pretreatment of the textile substrate, such as, for example, cellulose fibers and regenerated cellulose fibers, and also silk and wool, takes place with an aqueous alkaline liquor prior to printing. Fixing reactive dyes requires alkali, for example sodium carbonate, sodium bicarbonate, sodium acetate, trisodium phosphate, sodium silicate, sodium hydroxide, alkali donors such as, for example, sodium chloroacetate, sodium formate, hydrotropic substances such as, for example, urea, reduction inhibitors, such as, for example, sodium nitrobenzenesulfonates, and also thickeners to prevent flowing of the motifs when the printing ink is applied, examples thereof being sodium alginates, modified polyacrylates or highly etherified galactonnannans.

These pretreatment reagents are applied uniformly to the textile substrate in a defined amount, using suitable applicators, as for example with a 2- or 3-roll pad mangle, by contactless spraying technologies, by means of foam application, or with appropriately adapted inkjet technologies, and are subsequently dried.

After printing has taken place, the textile fiber material is dried at 120 to 150° C. and then fixed.

Fixing the inkjet prints produced with reactive dyes can be accomplished at room temperature, or with saturated steam, with superheated steam, with hot air, with microwaves, with infrared radiation, with laser beams or electron beams, or with other suitable energy transfer techniques.

A distinction is made between one- and two-phase fixing operations. In one-phase fixing, the chemicals needed for fixing are already on the textile substrate. In two-phase fixing, this pretreatment is unnecessary. Fixing requires only alkali, which, following inkjet printing, is applied prior to the fixing operation, without drying in between. Further additives such as urea or thickeners are redundant.

Following the fixing operation, the print is aftertreated, which is a prerequisite for good fastness properties, high brilliance, and an impeccable white ground.

The prints produced with the inks of the invention possess high color strength and a high fiber-dye bond stability, not only in the acidic range but also in the alkaline range, and also have good light fastness and very good wet fastness properties, such as fastness to washing, water, salt water, cross-dyeing, and perspiration, and also good fastness to pleating, hot pressing, and rubbing.

The dyes of the general formula (I) according to the invention furnish violet to blue dyeings and prints, and inkjet prints, on the materials specified.

The examples hereinbelow serve to illustrate the invention. The parts are parts by weight and the percentages are percent by weight, unless noted otherwise. The relationship between parts by weight and parts by volume is that of the kilogram to the liter. The compounds described by formula in the examples are written in the form of the sodium salts, since in general they are prepared and isolated in the form of their salts, preferably sodium salts or potassium salts, and used for dyeing in the form of their salts. The starting compounds specified in the examples below, especially the tabular examples, can be used in the synthesis in the form of the free acid or likewise in the form of their salts, preferably alkali metal salts, such as sodium salts or potassium salts.

EXAMPLE 1

34.1 parts of 2,5-dimethoxy-4-(β-sulfatoethylsulfonyl)aniline are suspended in 70 parts of ice/water and 18 parts of 30% strength hydrochloric acid, and diazotization is carried out by dropwise addition of 17.5 parts of 40% strength sodium nitrite solution.

After the excess nitrite has been removed using amidosulfonic acid solution, the resulting diazo suspension is pumped into an aqueous solution of 69.1 parts of the red monoazo dye of the formula (16-1)

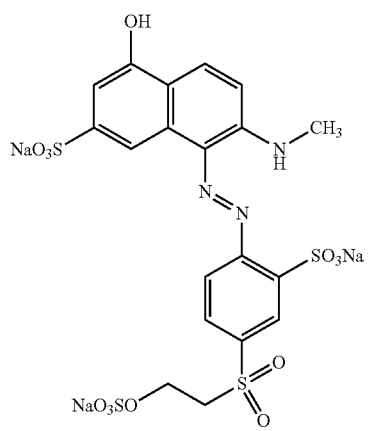

(16-1)

which has been obtained by diazotizing 36.1 parts of 2-amino-5-(β-sulfatoethylsulfonyl)-benzenesulfonic acid with 17.5 parts of 40% strength sodium nitrite solution in an acidic medium and carrying out subsequent coupling to 25.3 parts of 4-hydroxy-7-(methyl-amino)-naphthalene-2-sulfonic acid at a pH of 1-1.5. Subsequently, below 25° C., sodium carbonate is used to set a pH of 5-6, and the mixture is held for approximately 1 h until the coupling reaction is at an end. The resultant aqueous solution of the bluish-red disazo dye of the formula (13-1)

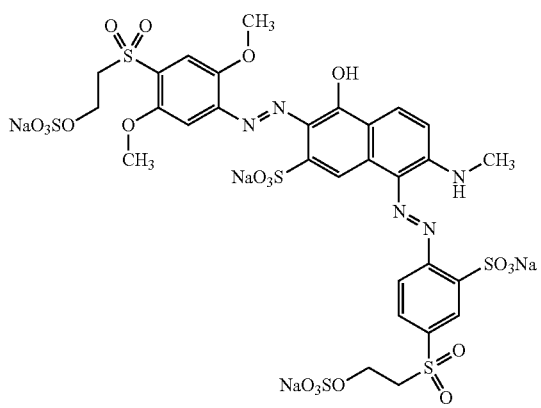

(13-1)

(having an absorption maximum at 548 nm) is subsequently admixed with 27.5 parts of copper(II) sulfate pentahydrate and is heated at reflux (100-102° C.) for 16-24 h at a pH of 3.5-5.5.

The blue disazo dye (I-1)

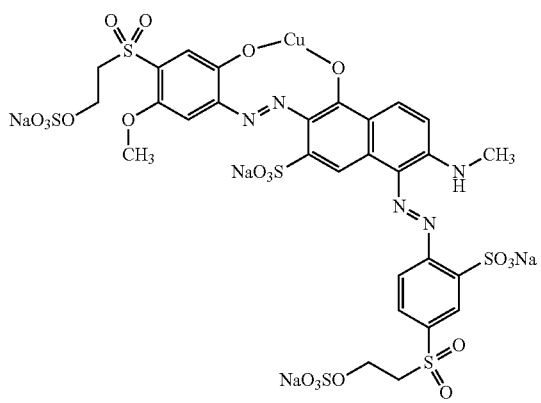

(I-1)

formed after the end of the coppering reaction has an absorption maximum of 580 nm and is present as a mixture of the ester forms and vinyl forms. It can be isolated by salting out with sodium chloride or potassium chloride, or by evaporation under reduced pressure, or by spray drying. Alternatively the dye solution obtained can also be buffered by addition of a phosphate buffer at pH 5.5-6 and adjusted by further dilution or concentration as a liquid product of defined strength.

The resulting dye of the invention, under the dyeing conditions customary for reactive dyes, affords blue dyeings and prints having good all-round fastness properties, on cotton, for example.

EXAMPLE 2

28.1 parts of 4-(β-sulfatoethylsulfonyl)-aniline are suspended in 70 parts of ice/water and 18 parts of 30% strength hydrochloric acid and diazotized by dropwise addition of 17.5 parts of 40% strength sodium nitrite solution. Following removal of the excess nitrite with amidosulfonic acid solution, the resulting diazo suspension is pumped into an aqueous solution of 69.1 parts of the red monoazo dye of the formula (16-1), which was obtained by diazotizing 36.1 parts of 2-amino-5-(β-sulfatoethylsulfonyl)-benzenesulfonic acid with 17.5 parts of 40% strength sodium nitrite solution in an acidic medium, followed by coupling to 25.3 parts of 4-hydroxy-7-(methyl-amino)-naphthalene-2-sulfonic acid at a pH of 1-1.5. Subsequently, at below 25° C., a pH of 5 is set using sodium carbonate, and the batch is held for about 1 h until the coupling reaction is at an end. The resulting aqueous solution of the brown-red disazo dye of the formula (13-2)

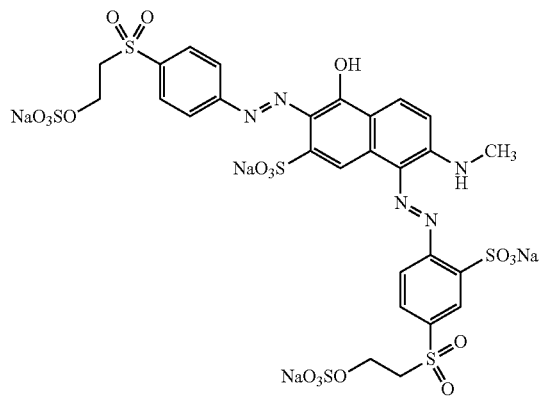

(13-2)

(absorption maximum 522 nm) is subsequently cooled to 10° C. by addition of ice. 25 parts of copper(II) sulfate pentahydrate are added and at a pH of 3.5-4.5 40 parts of a 35% strength hydrogen peroxide solution are added dropwise over 15 minutes. Stirring is continued at 15-20° C. for 15-30 minutes and then a pH of 5-6 is set by slow addition of sodium carbonate.

The blue-violet disazo dye obtained after the end of the coppering reaction, of the formula (I-2),

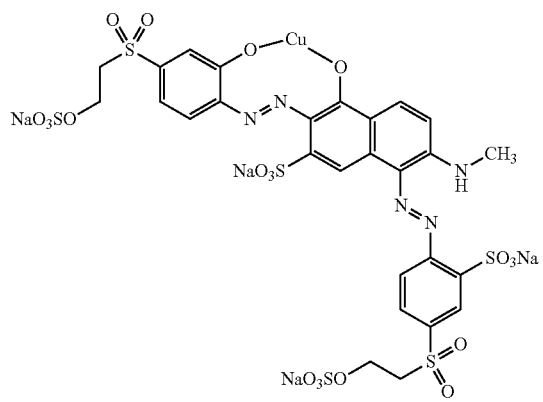

(I-2)

has an absorption maximum of 555 nm and can be isolated by salting out with sodium chloride or potassium chloride or alternatively by evaporation under reduced pressure or by spray drying.

Under the dyeing conditions customary for reactive dyes, on cotton, for example, it affords blue-violet dyeings and prints having good all-round fastness properties.

EXAMPLE 3 a) 28.1 parts of 4-(β-sulfatoethylsulfonyl)-aniline are suspended in 70 parts of ice/water and 18 parts of 30% strength hydrochloric acid and diazotized by dropwise addition of 17.5 parts of 40% strength sodium nitrite solution. Following removal of the excess nitrite with amidosulfonic acid solution, the resulting diazo suspension is admixed with an aqueous solution of 33.3 parts of 4-hydroxy-7-(sulfomethyl-amino)-naphthalene-2-sulfonic acid, which has been obtained by reaction of 23.9 parts of 7-amino-4-hydroxy-naphthalene-2-sulfonic acid with 15 parts of formaldehyde-sodium bisulfite in aqueous medium at a pH of 5.5-6 and at 45° C., and is adjusted to a pH of 1.5 using solid sodium hydrogen carbonate. This is followed by stirring at a pH of 1.5 and at 15-20° C. until the acidic coupling reaction is at an end.

b) In a separate reaction vessel, 38 parts of 3-amino-2-hydroxy-5-(β-sulfatoethylsulfonyl)-benzenesulfonic acid are suspended in 75 parts of ice/water and 18 parts of 30% strength hydrochloric acid and diazotized by dropwise addition of 18 parts of 40% strength sodium nitrite solution. Following removal of the excess nitrite with amidosulfonic acid, this diazo suspension is added dropwise to the first coupling stage from a) and, at below 25° C., a pH of 6.5-7.5 is set using sodium carbonate. After coupling has taken place, 22 parts of copper hydroxide carbonate ($CuCO_3 \times Cu(OH)_2$) are added and stirring is continued for 1-2 hours until coppering is at an end. The resultant violet disazo dye of the formula (I-3)

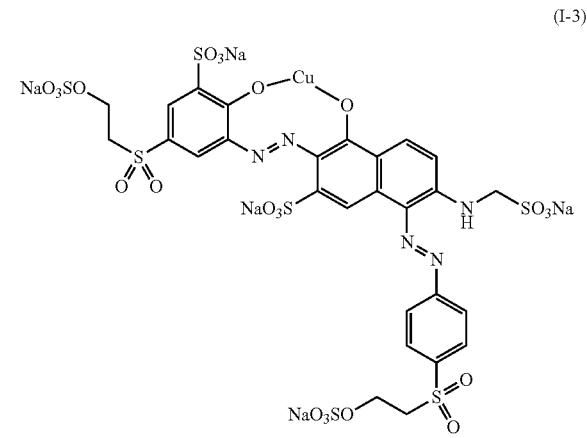

(I-3)

has an absorption maximum of 540 nm and can be isolated by salting out with sodium chloride or potassium chloride or alternatively by evaporation under reduced pressure or by spray drying.

Under the dyeing conditions customary for reactive dyes, on cotton, for example, it affords violet dyeings and prints having good all-round fastness properties.

EXAMPLE 4

20.5 parts of 3-amino-4-methoxy-benzenesulfonic acid are suspended in 80 parts of ice/water and 18 parts of 30% strength hydrochloric acid and diazotized by dropwise addition of 17.5 parts of 40% strength sodium nitrite solution. Following removal of the excess nitrite with amidosulfonic acid solution, the resulting diazo suspension is pumped into an aqueous solution of 69.1 parts of the red monoazo dye of the formula (16-1), obtained as described in example 1. Then the pH is set at 7-8 using sodium carbonate and is maintained at 20-25° C. until the end of the coupling reaction. The resulting aqueous solution of the bluish-red disazo dye of the formula (13-3)

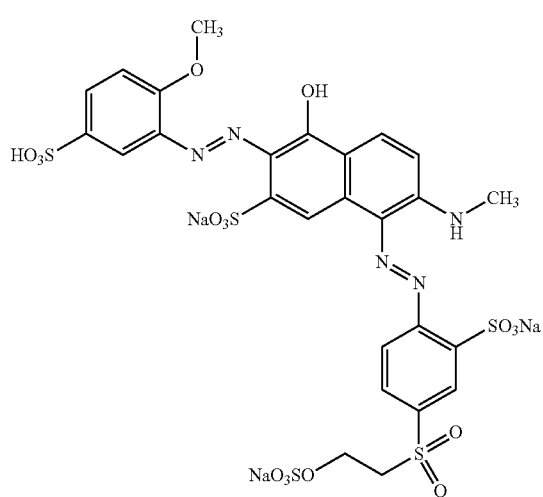

(13-3)

(having an absorption maximum of 530 nm) is subsequently admixed with 27.5 parts of copper(II) sulfate pentahydrate and is heated at reflux (100-102° C.) for 16-24 h at a pH of 3.5-5.5.

The violet disazo dye (I-4)

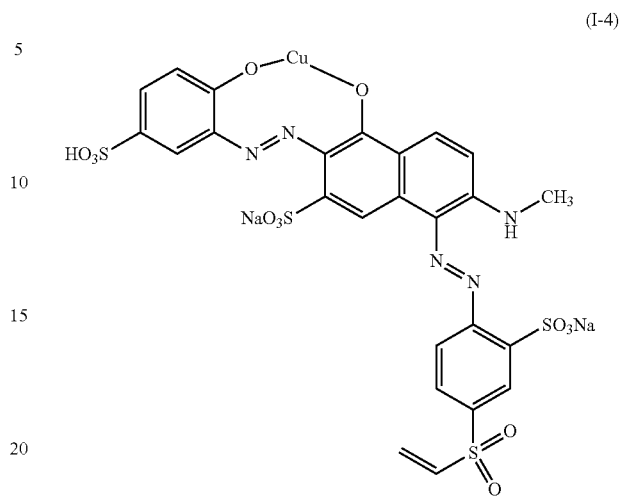

(I-4)

which is formed after the end of the coppering reaction has an absorption maximum of 552 nm. It can be isolated by salting out with sodium chloride or potassium chloride or by evaporation under reduced pressure or by spray drying.

The resulting dye of the invention, under the dyeing conditions customary for reactive dyes, on cotton, for example, affords violet dyeings and prints having good all-round fastness properties.

EXAMPLES 5 TO 67

The examples below describe further dyes of the general formula (I) according to the invention which are preparable in accordance with examples 1 to 4 and which are each given in the form of the sodium salts (M=Na). In accordance with the dyeing methods customary for reactive dyes, on cotton, for example, the dyes afford violet to blue dyeings.

| Example | Dye of the formula (I) | Dyeing on cotton |
| --- | --- | --- |
| 5 | | red-violet |

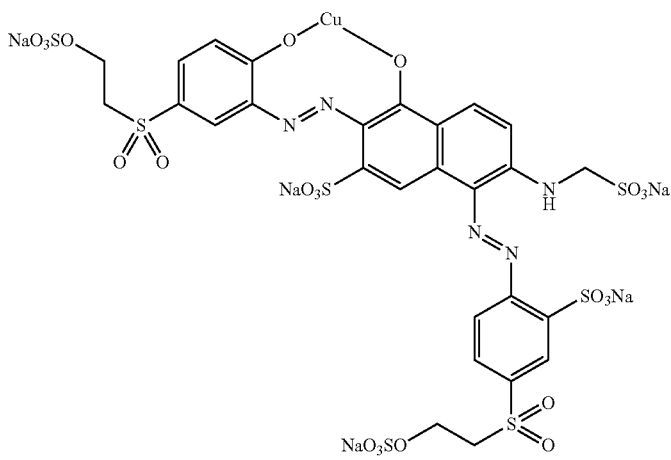

(I-5)

-continued
| Example | Dye of the formula (I) | Dyeing on cotton |
|---|---|---|
| 6 | 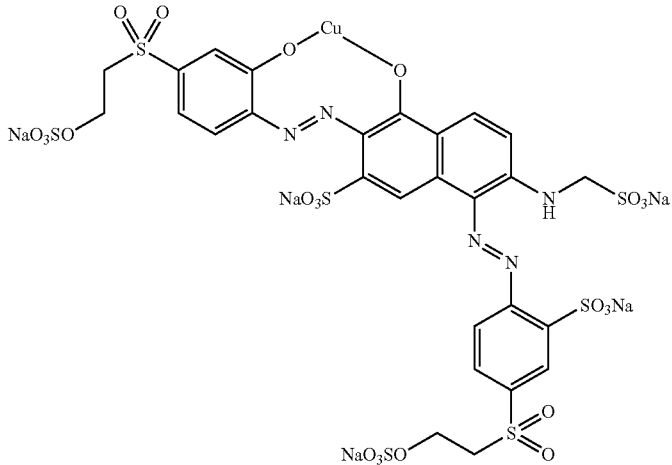 (I-6) | red-violet |
| 7 | 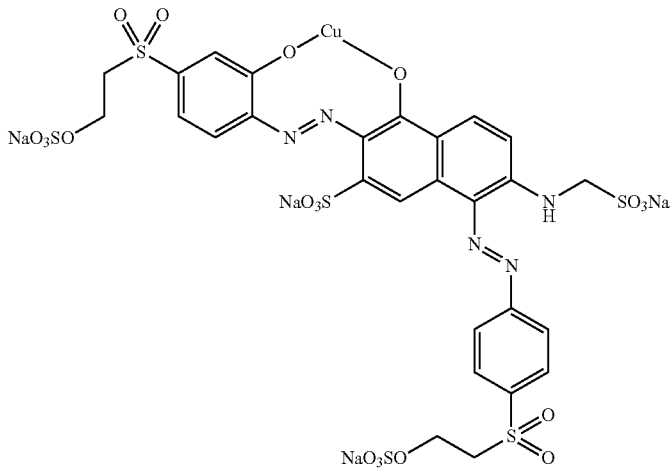 (I-7) | red-violet |
| 8 | 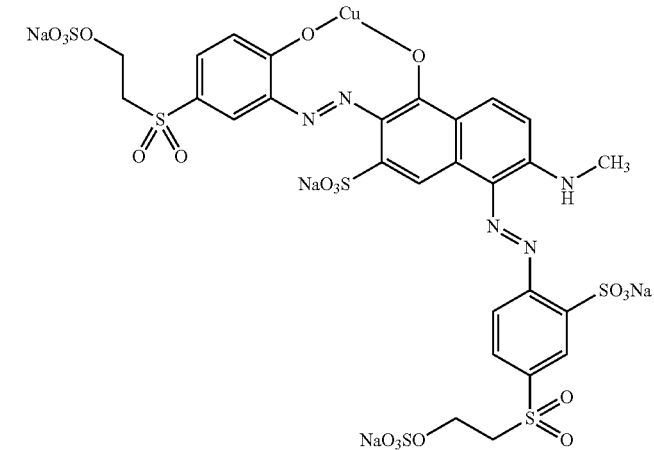 (I-8) | violet |

-continued
| Example | Dye of the formula (I) | Dyeing on cotton |
|---|---|---|
| 9 | 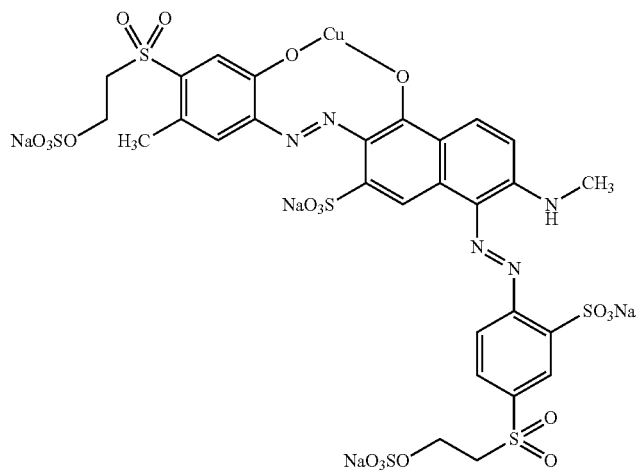<br>(I-9) | blue |
| 10 | 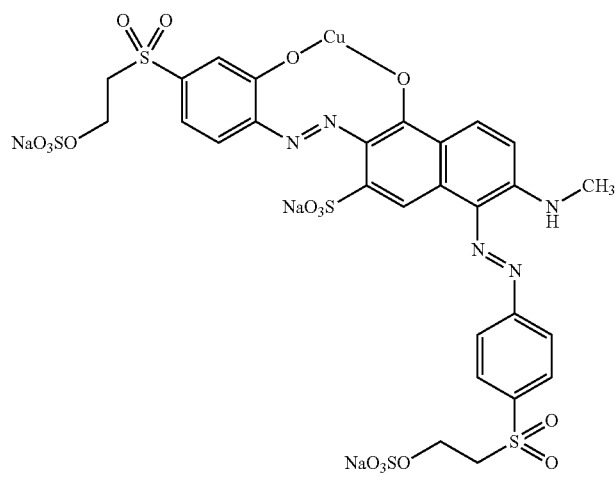<br>(I-10) | violet |
| 11 | 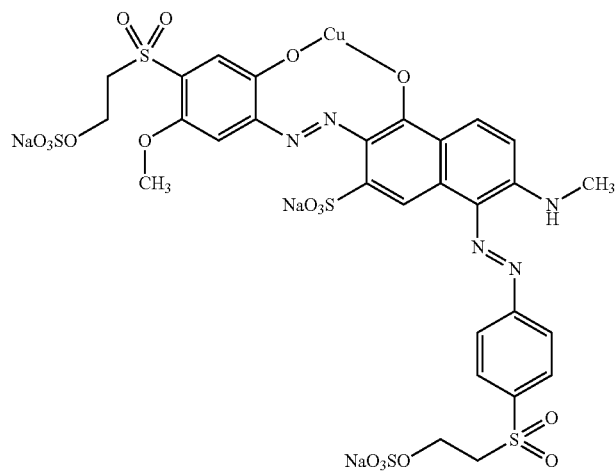<br>(I-11) | blue |

| Example | Dye of the formula (I) | Dyeing on cotton |
|---|---|---|
| 12 | 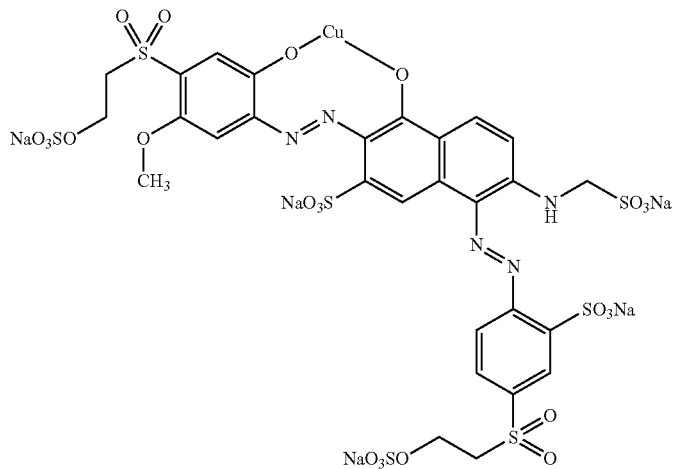<br>(I-12) | blue-violet |
| 13 | 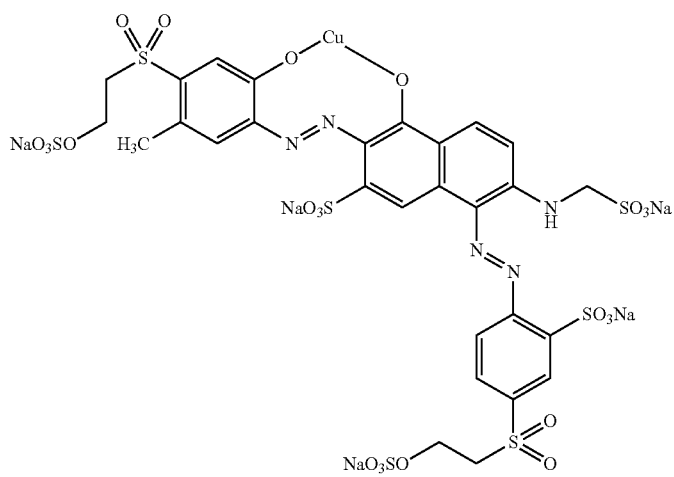<br>(I-13) | blue-violet |
| 14 | 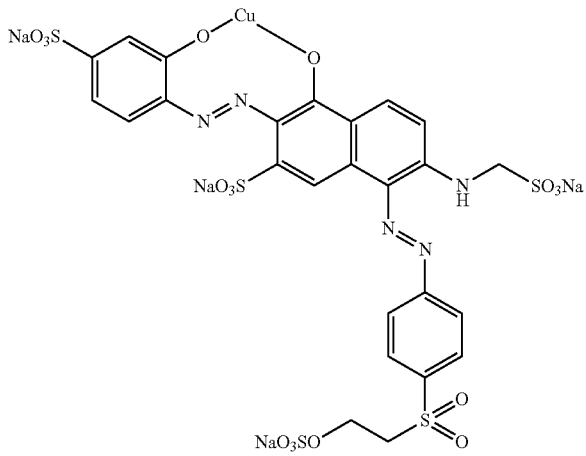<br>(I-14) | red-violet |

| Example | Dye of the formula (I) | Dyeing on cotton |
|---|---|---|
| 15 | 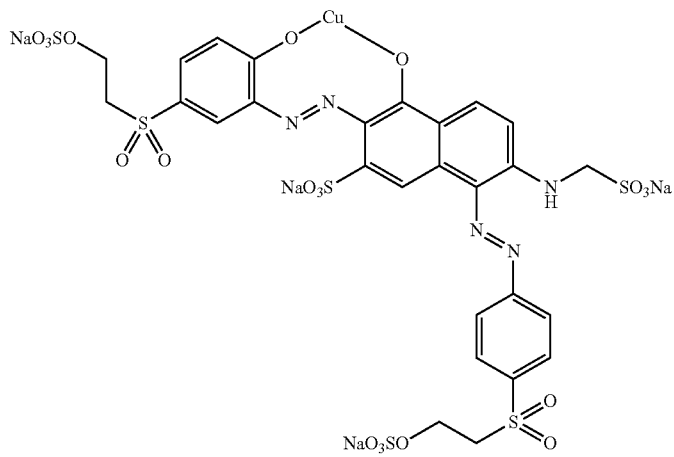<br>(I-15) | red-violet |
| 16 | 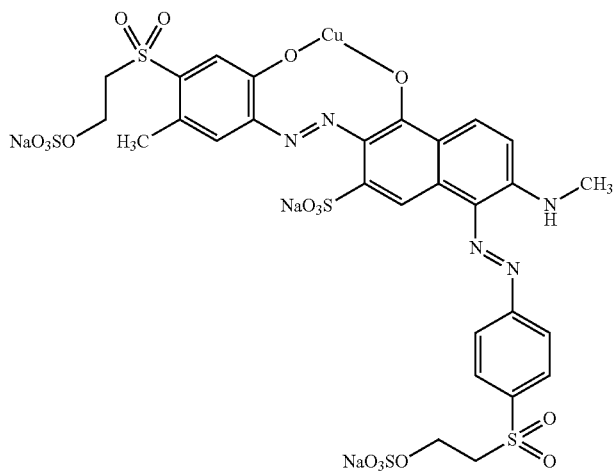<br>(I-16) | blue |
| 17 | 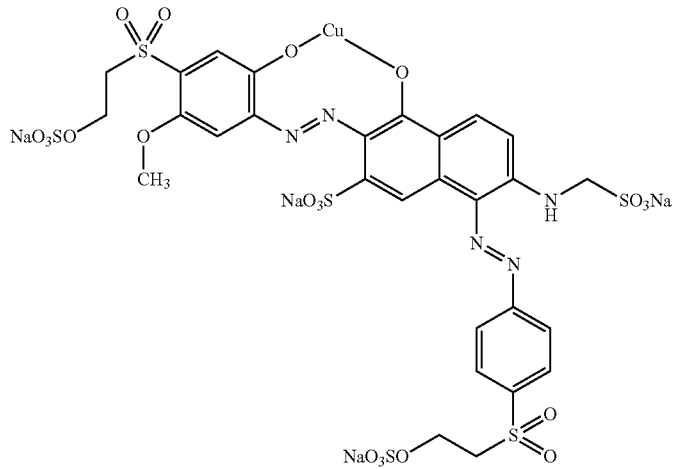<br>(I-17) | violet |

-continued
| Example | Dye of the formula (I) | Dyeing on cotton |
|---|---|---|
| 18 | 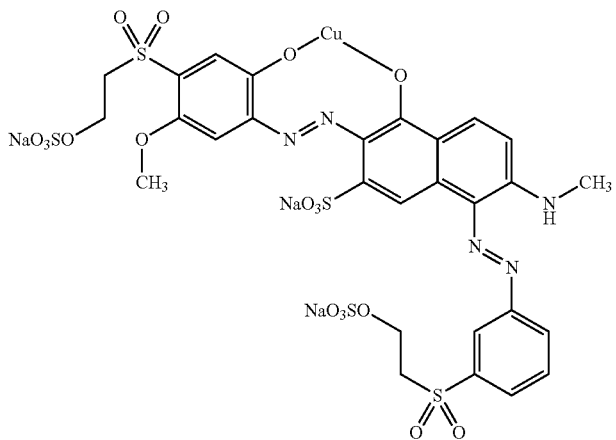<br>(I-18) | blue |
| 19 | 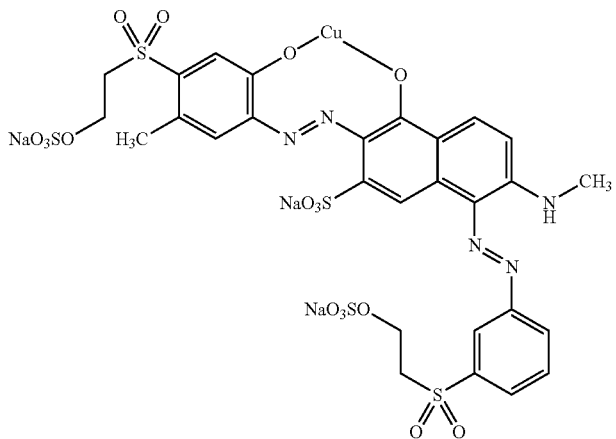<br>(I-19) | blue |
| 20 | 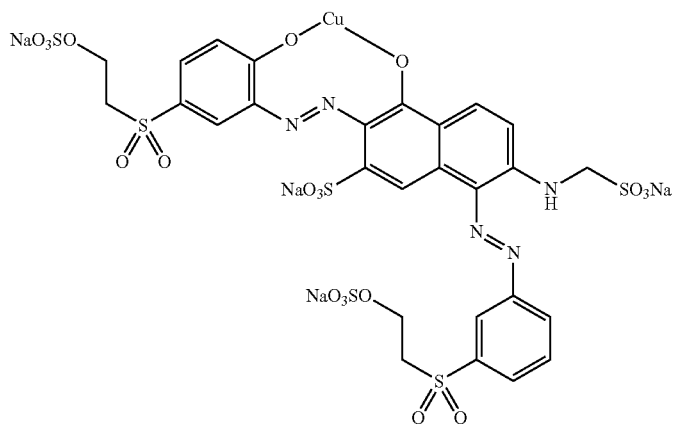<br>(I-20) | red-violet |

| Example | Dye of the formula (I) | Dyeing on cotton |
|---|---|---|
| 21 | 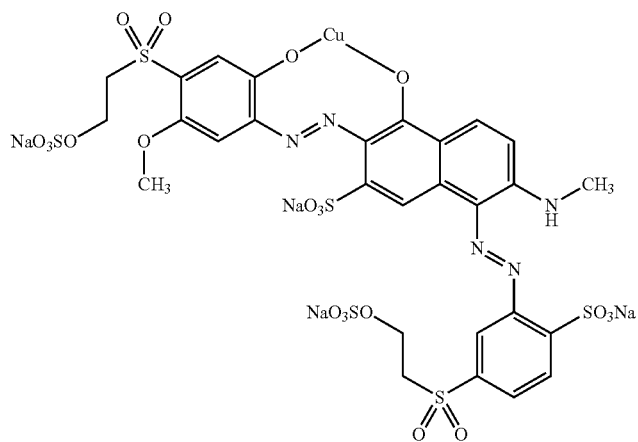<br>(I-21) | blue |
| 22 | 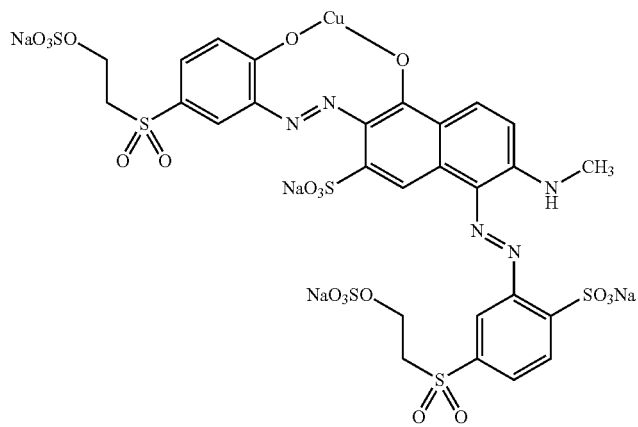<br>(I-22) | violet |
| 23 | 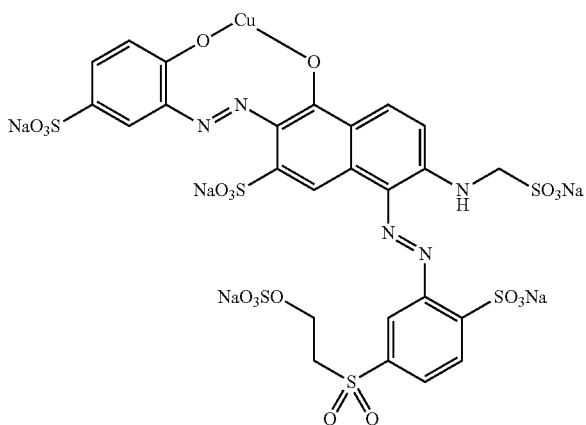<br>(I-23) | red-violet |

| Example | Dye of the formula (I) | Dyeing on cotton |
|---|---|---|
| 24 | 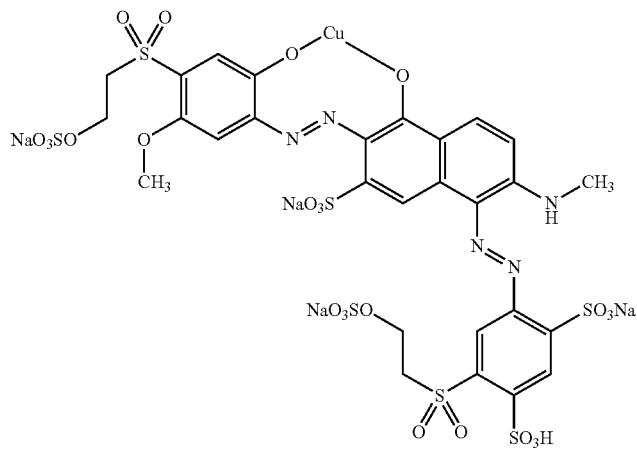 (I-24) | blue |
| 25 | 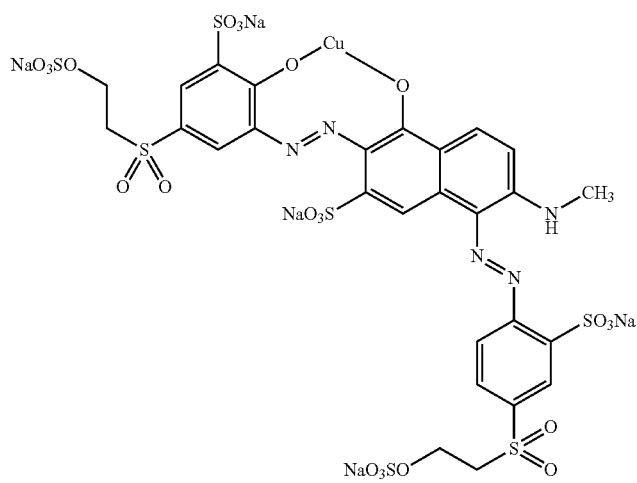 (I-25) | violet |
| 26 | 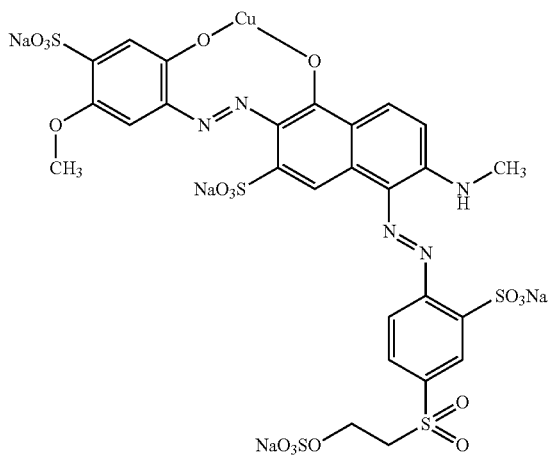 (I-26) | blue-violet |

| Example | Dye of the formula (I) | Dyeing on cotton |
|---|---|---|
| 27 | 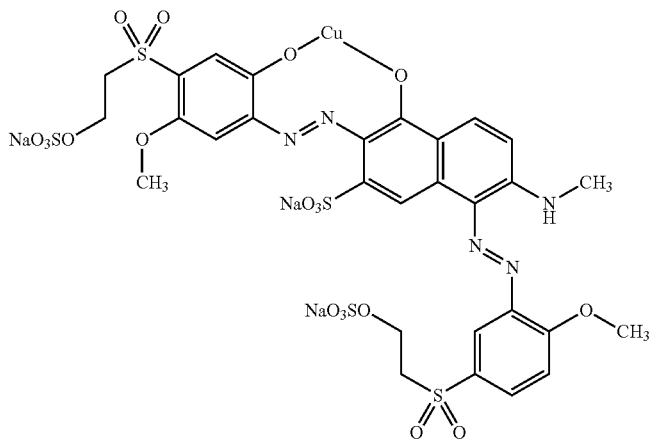<br>(I-27) | blue |
| 28 | 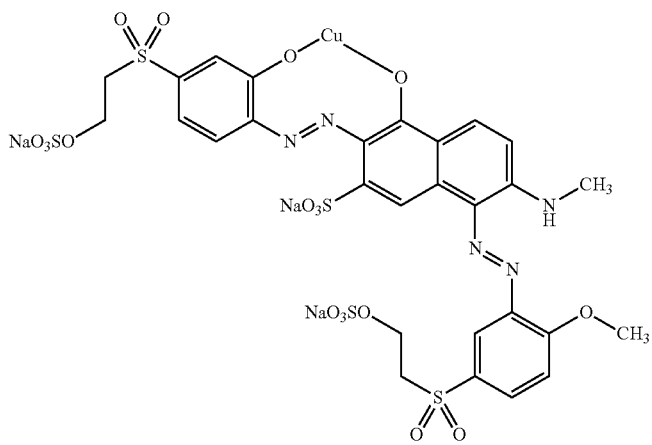<br>(I-28) | violet |
| 29 | 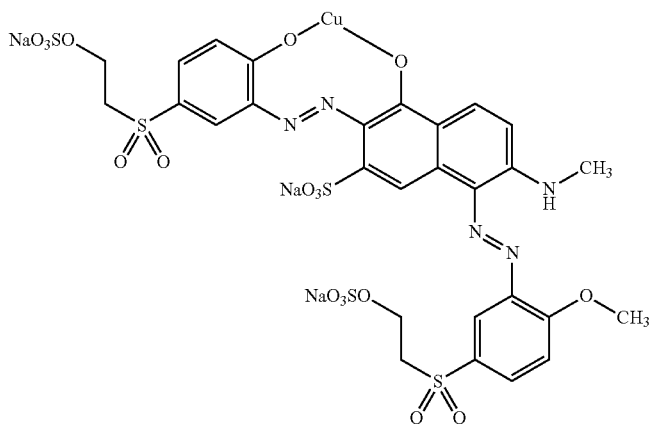<br>(I-29) | red-violet |

| Example | Dye of the formula (I) | Dyeing on cotton |
|---|---|---|
| 30 | 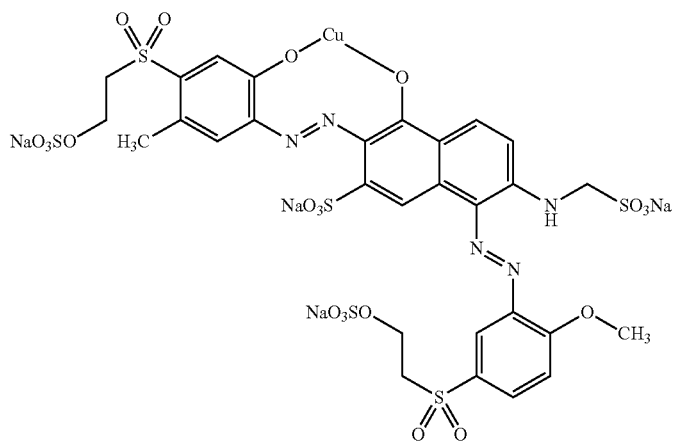<br>(I-30) | blue-violet |
| 31 | 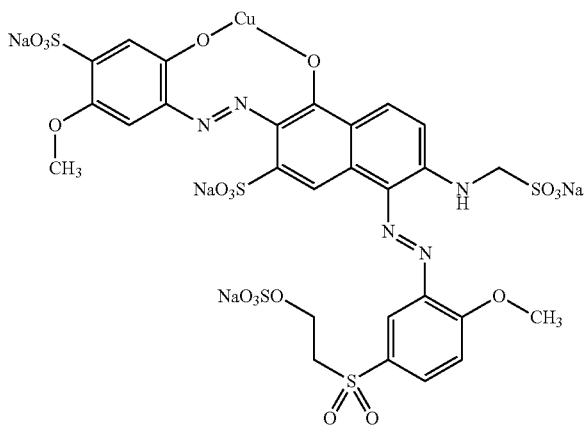<br>(I-31) | violet |
| 32 | 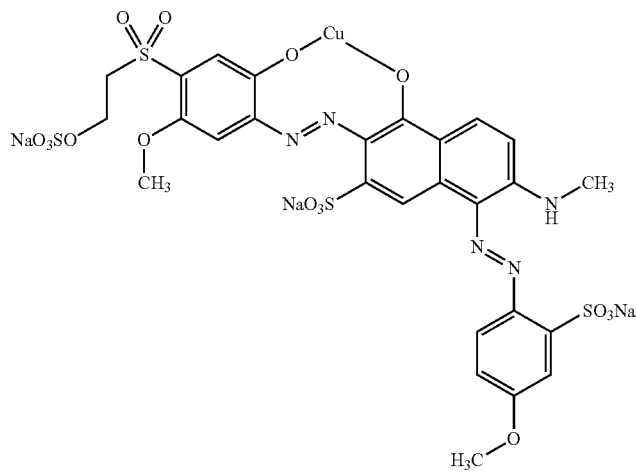<br>(I-32) | blue |

| Example | Dye of the formula (I) | Dyeing on cotton |
|---|---|---|
| 33 | 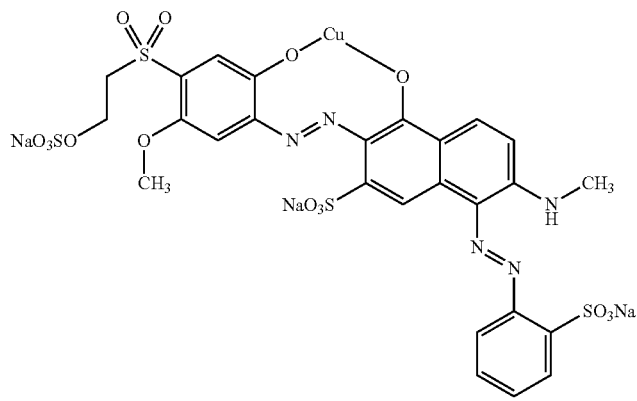<br>(I-33) | blue-violet |
| 34 | 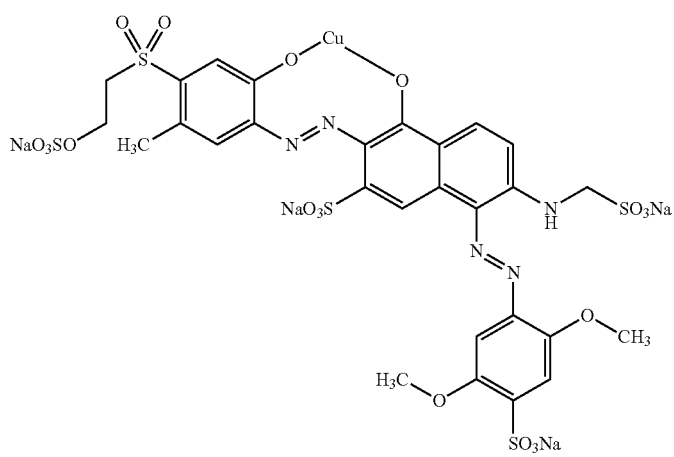<br>(I-34) | blue-violet |
| 35 | 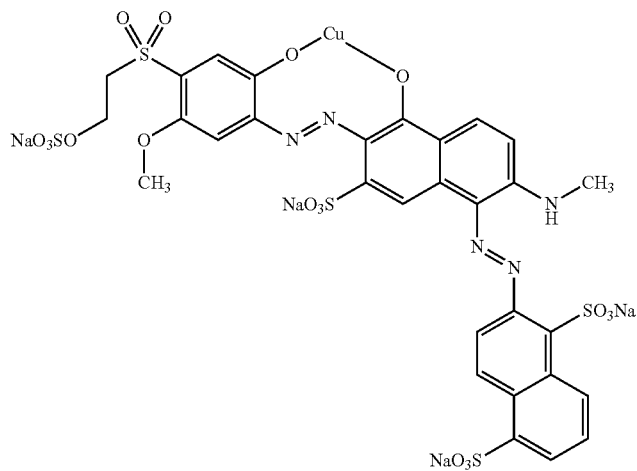<br>(I-35) | blue |

| Example | Dye of the formula (I) | Dyeing on cotton |
|---------|------------------------|------------------|
| 36 | 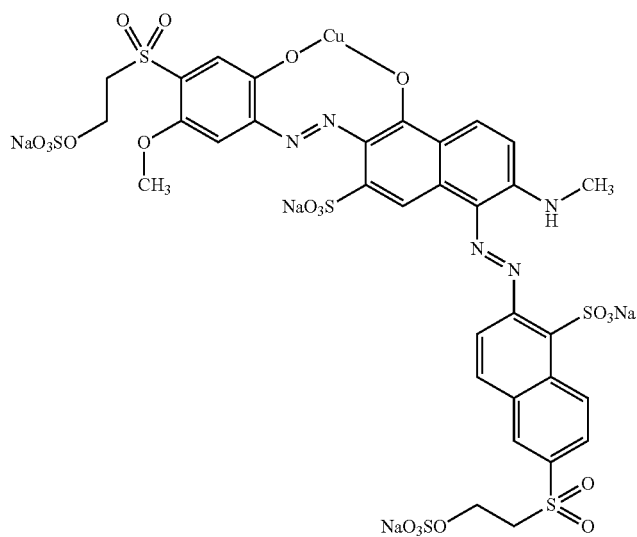<br>(I-36) | blue |
| 37 | 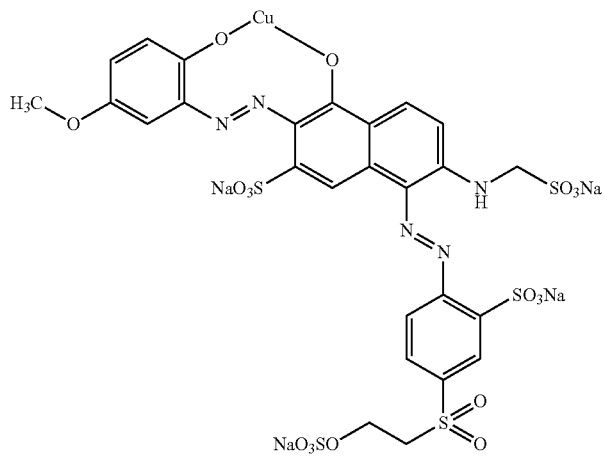<br>(I-37) | blue-violet |
| 38 | 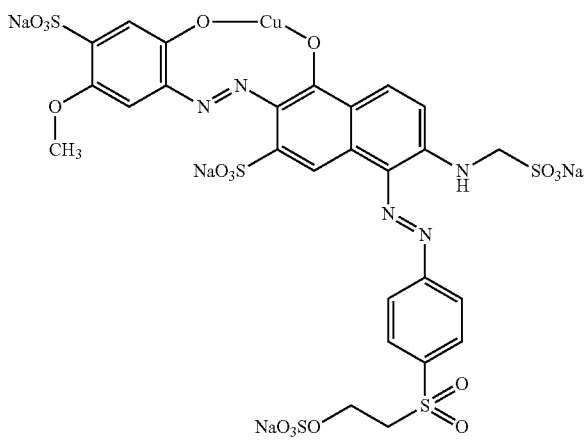<br>(I-38) | violet |

| Example | Dye of the formula (I) | Dyeing on cotton |
|---|---|---|
| 39 | 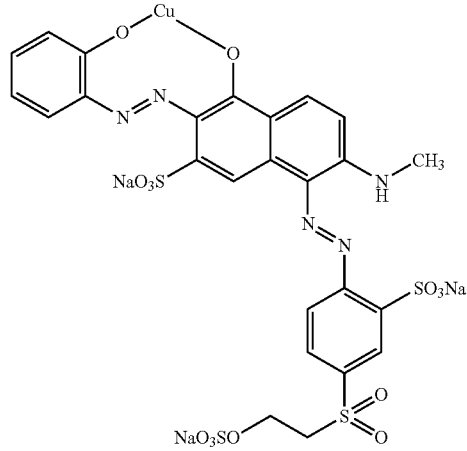 (I-39) | violet |
| 40 | 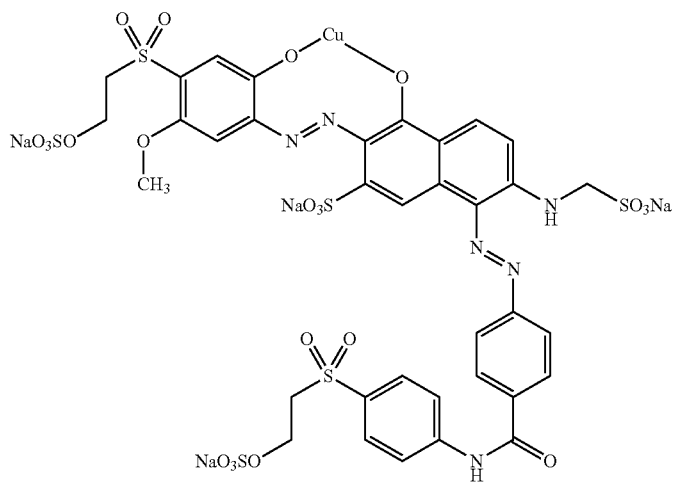 (I-40) | blue-violet |
| 41 | 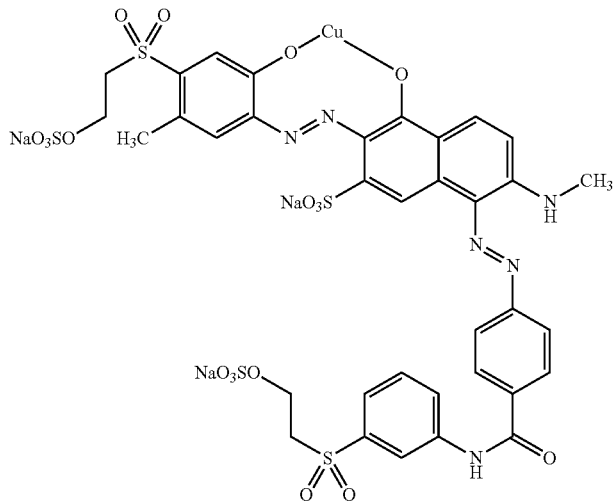 (I-41) | blue |

| Example | Dye of the formula (I) | Dyeing on cotton |
|---|---|---|
| 42 | 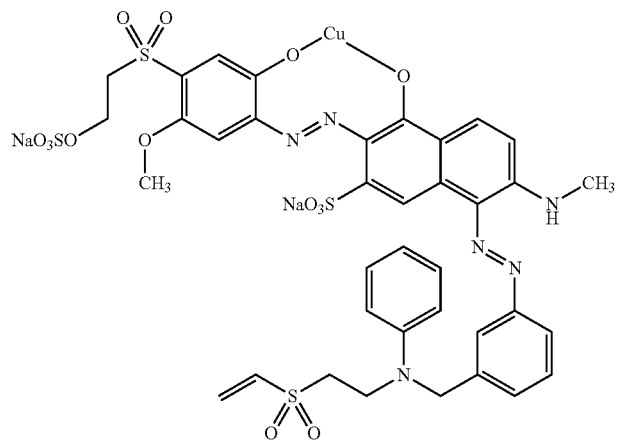<br>(I-42) | blue |
| 43 | 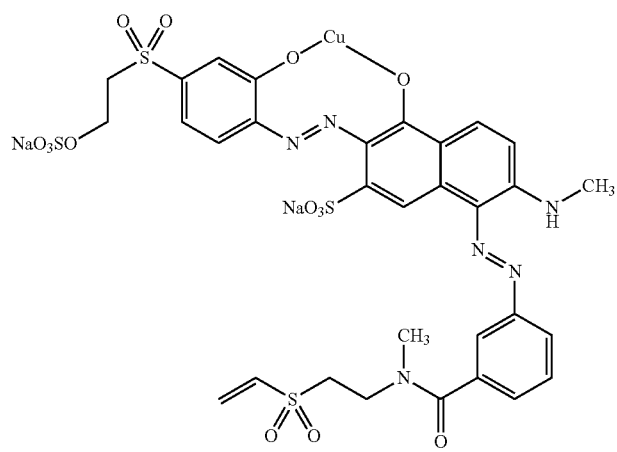<br>(I-43) | violet |
| 44 | 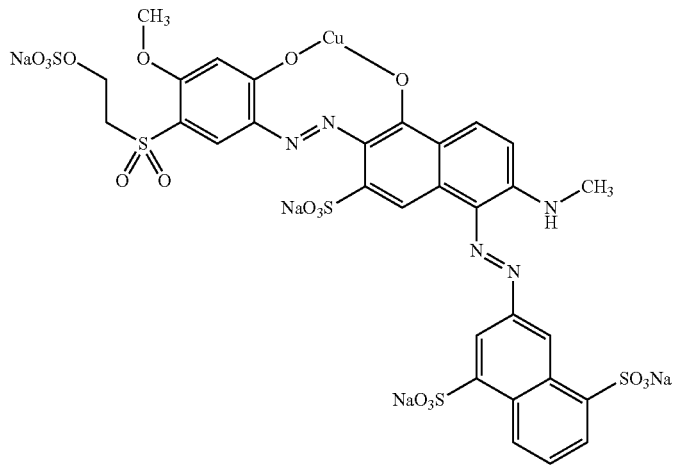<br>(I-44) | violet |

| Example | Dye of the formula (I) | Dyeing on cotton |
|---|---|---|
| 45 | (I-45) | violet |
| 46 | (I-46) | violet |
| 47 | (I-47) | blue-violet |

-continued
| Example | Dye of the formula (I) | Dyeing on cotton |
|---|---|---|
| 48 | 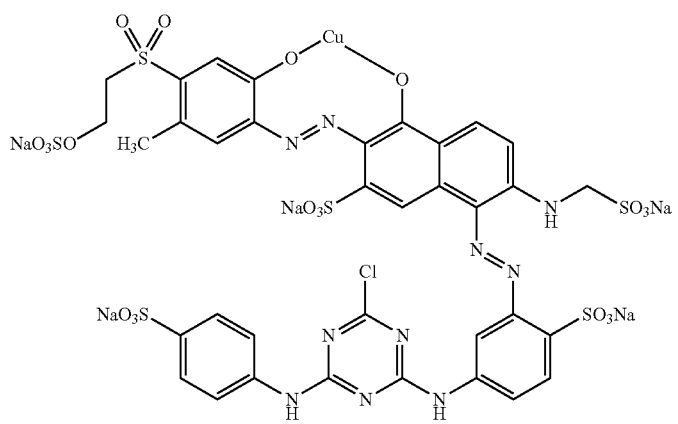 (I-48) | blue-violet |
| 49 | 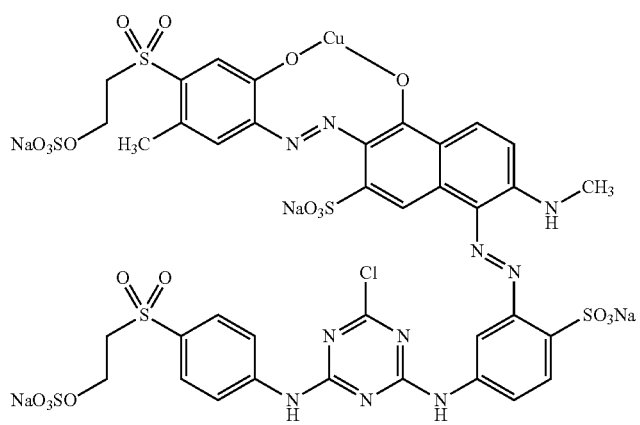 (I-49) | blue-violet |
| 50 | 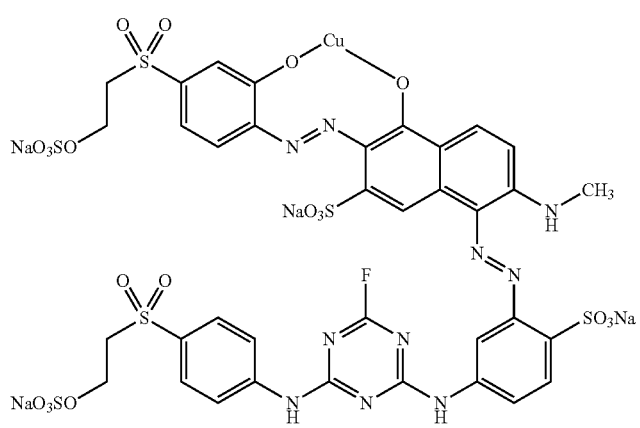 (I-50) | violet |

| Example | Dye of the formula (I) | Dyeing on cotton |
|---|---|---|
| 51 | 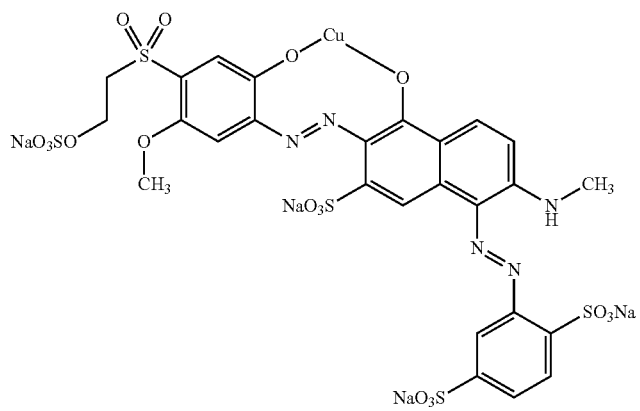<br>(I-51) | blue-violet |
| 52 | 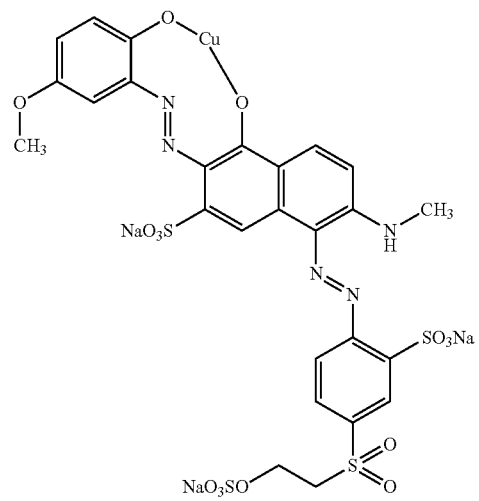<br>(I-52) | violet |
| 53 | 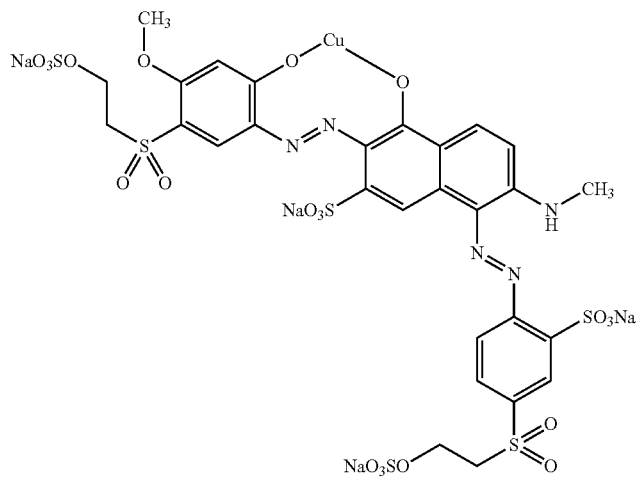<br>(I-53) | violet |

| Example | Dye of the formula (I) | Dyeing on cotton |
|---|---|---|
| 54 | 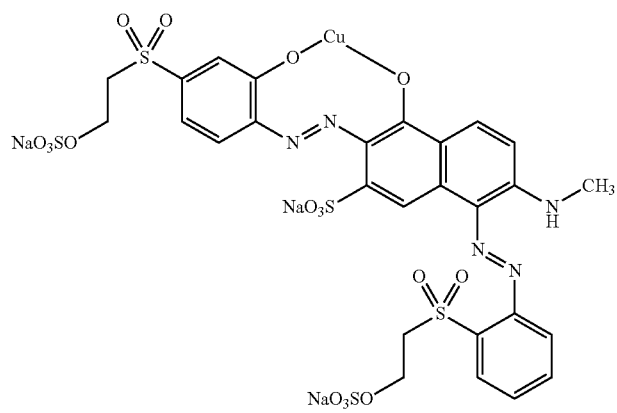 (I-54) | blue-violet |
| 55 | 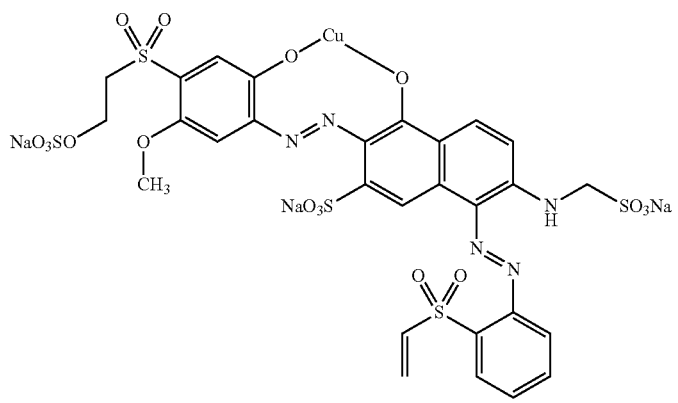 (I-55) | blue-violet |
| 56 | 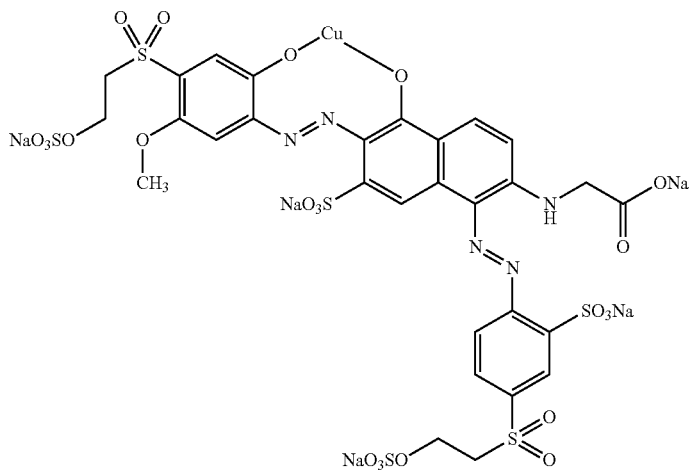 (I-56) | blue |

| Example | Dye of the formula (I) | Dyeing on cotton |
|---------|------------------------|------------------|
| 57 | 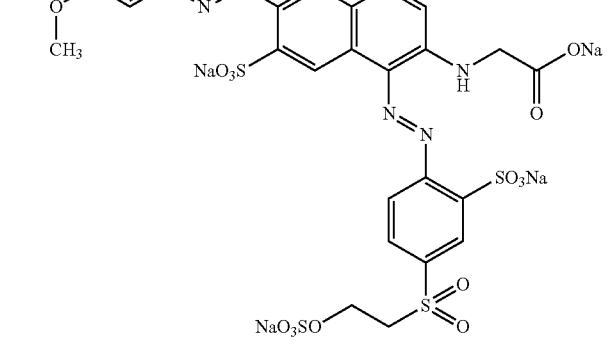<br>(I-57) | blue |
| 58 | 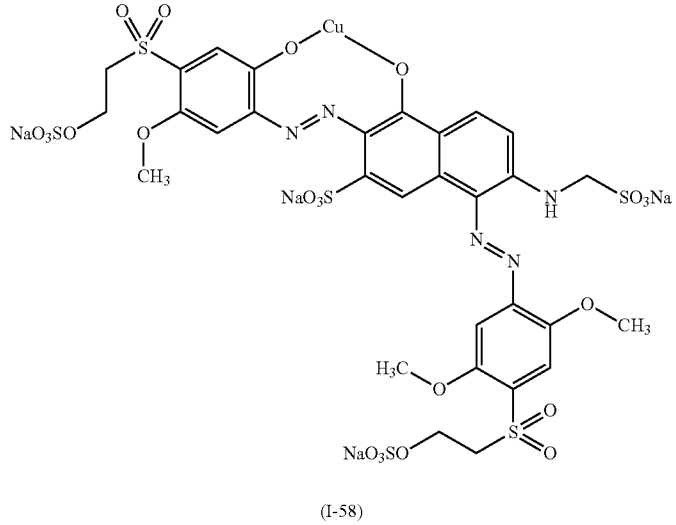<br>(I-58) | blue-violet |
| 59 | 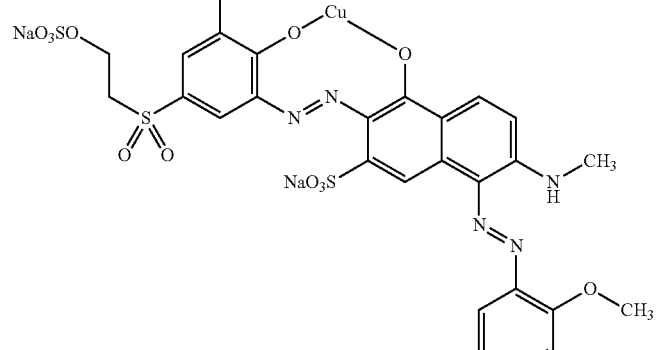<br>(I-59) | blue-violet |

| Example | Dye of the formula (I) | Dyeing on cotton |
|---|---|---|
| 60 | 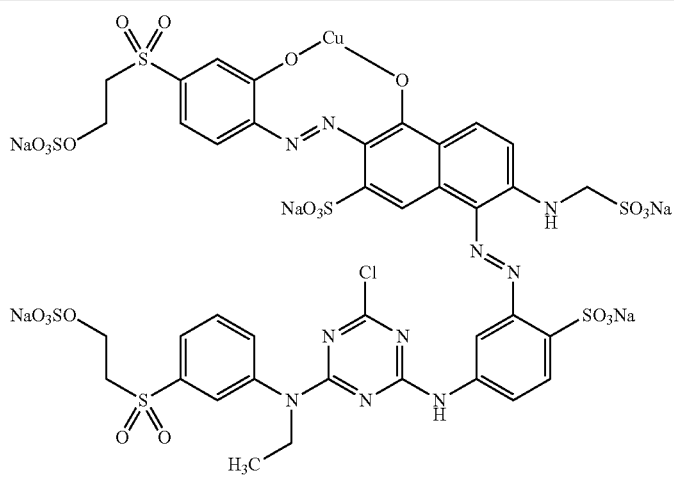 (I-60) | violet |
| 61 | 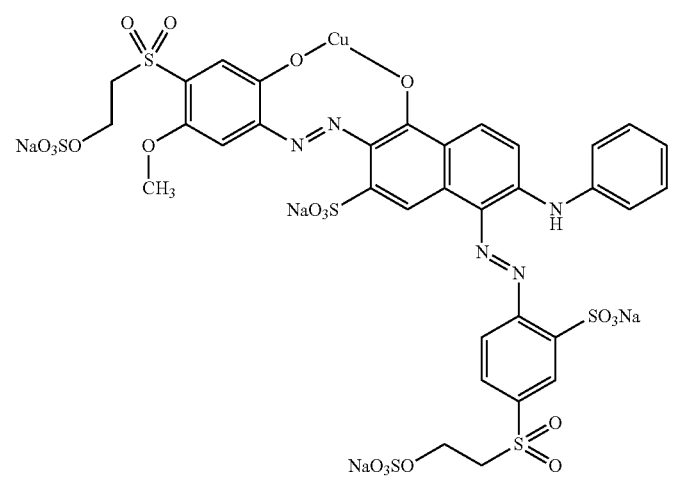 (I-61) | blue |
| 62 | 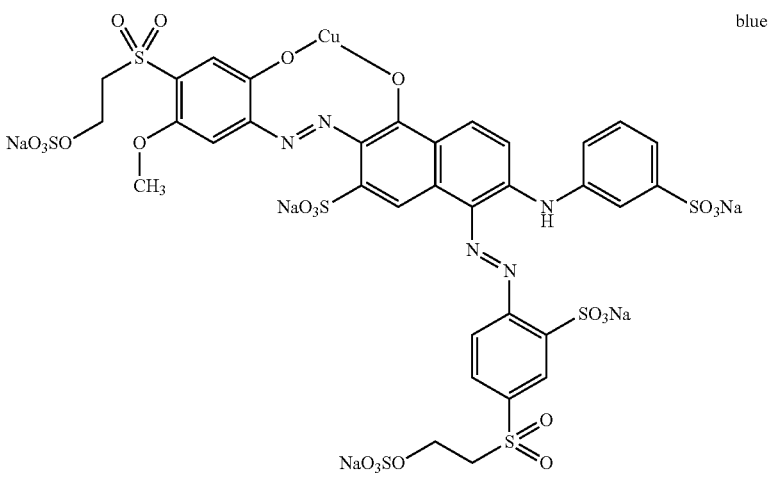 (I-62) | blue |

| Example | Dye of the formula (I) | Dyeing on cotton |
|---|---|---|
| 63 | 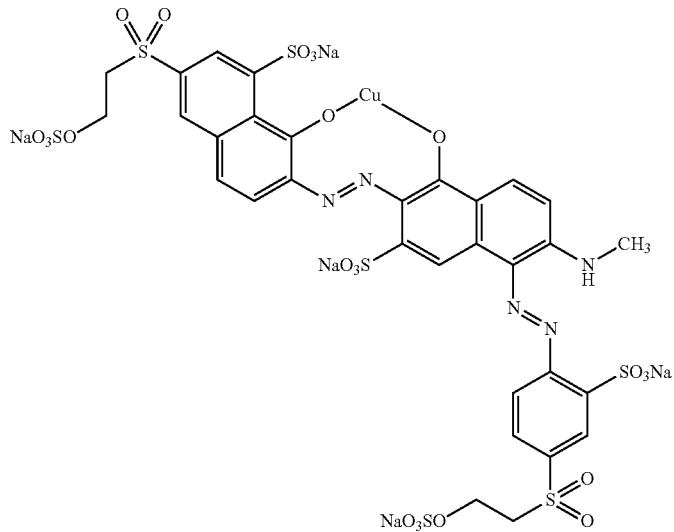 (I-63) | blue |
| 64 | 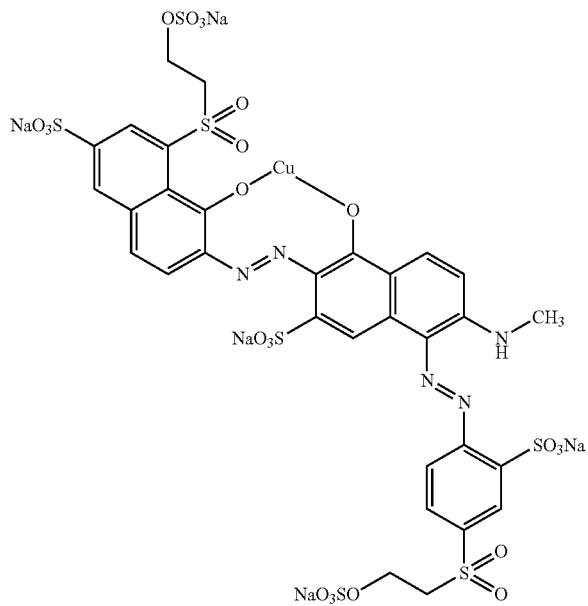 (I-64) | blue |

| Example | Dye of the formula (I) | Dyeing on cotton |
|---|---|---|
| 65 | 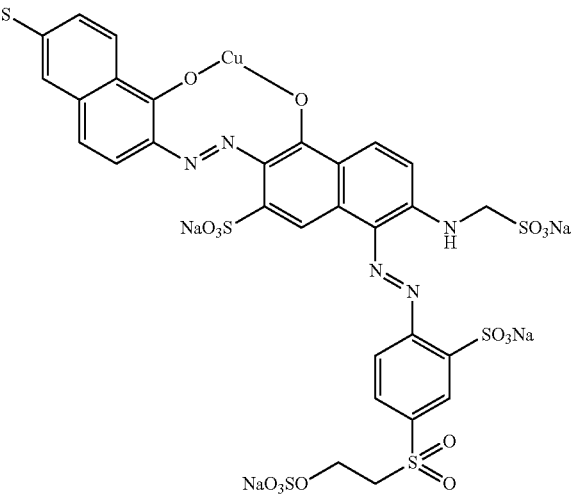<br>(I-65) | violet |
| 66 | 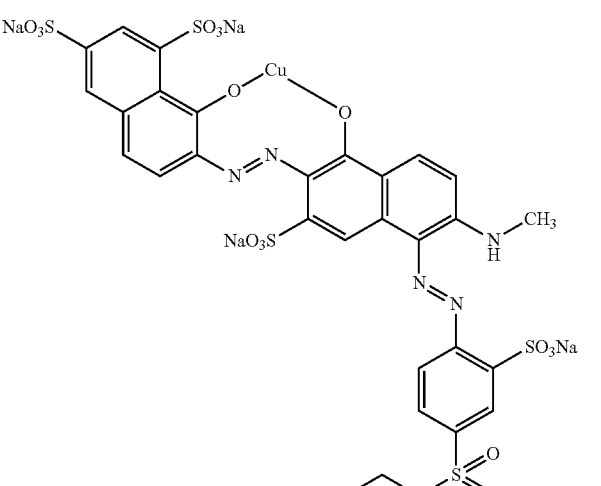<br>(I-66) | blue-violet |
| 67 | 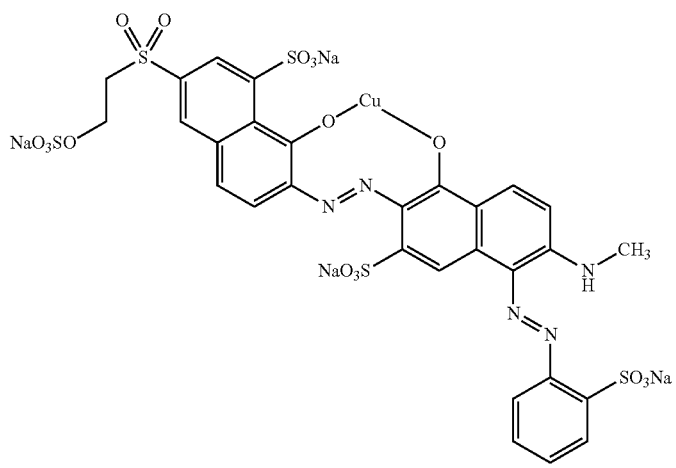<br>(I-67) | blue-violet |

APPLICATION EXAMPLE 1

2 parts of the dye obtained in example 1 and 50 parts of sodium chloride are dissolved in 999 parts of water, and 5 parts of sodium carbonate, 0.7 part of sodium hydroxide (in the form of a 32.5% strength aqueous solution) and, if necessary, 1 part of a wetting agent are added. This dyebath is entered with 100 g of a woven cotton fabric. The temperature of the dyebath is maintained at 25° C. for 10 minutes to start with, then raised over 30 minutes to the final temperature (40-80° C.) and held at that temperature for a further 60-90 minutes. Thereafter the dyed goods are rinsed first for 2 minutes with drinking water and subsequently for 5 minutes with deionized water. The dyed goods are neutralized at 40° C. in 1000 parts of an aqueous solution containing 1 part of 50% strength acetic acid for 10 minutes. This is followed by rinsing with deionized water at 70° C. and then by soaping off at the boil for 15 minutes with a laundry detergent, rinsing again, and drying. This gives a strongly colored blue dyeing having very good fastness properties.

APPLICATION EXAMPLE 2

4 parts of the dye of example 1 and 50 parts of sodium chloride are dissolved in 998 parts of water, and 5 parts of sodium carbonate, 2 parts of sodium hydroxide (in the form of a 32.5% strength aqueous solution) and, if necessary, 1 part of a wetting agent are added. This dyebath is entered with 100 g of a woven cotton fabric. Further treatment is as stated in application example 1. This gives a strongly colored blue dyeing having very good fastness properties.

APPLICATION EXAMPLE 3

A sheetlike textile structure composed of mercerized cotton is padded with a liquor containing 35 g/l of calcined sodium carbonate, 100 g/l of urea and 150 g/l of a low-viscosity Na alginate solution (6%), and then dried. The liquor pickup is 70%.

The textile thus pretreated is printed with an aqueous ink containing
2% of the dye of example 1
20% of sulfolane
0.01% of Mergal K9N and
77.99% of water
using a drop-on-demand (bubble-jet) inkjet print head. The print is dried fully. Fixing is accomplished by means of saturated steam at 102° C. for 8 minutes. Then the print is given a warm rinse, subjected to a fastness wash with hot water at 95° C., rinsed warm, and then dried. This gives a blue print having very good service fastnesses.

APPLICATION EXAMPLE 4

A sheetlike textile structure composed of mercerized cotton is padded with a liquor containing 35 g/l of calcined sodium carbonate, 100 g/l of urea and 150 g/l of a low-viscosity Na alginate solution (6%), and then dried. The liquor pickup is 70%. The textile thus pretreated is printed with an aqueous ink containing
2% of the dye of example 1
15% of N-methylpyrrolidone
0.01% of Mergal K9N and
76.99% of water
using a drop-on-demand (bubble-jet) inkjet print head. The print is dried fully. Fixing is accomplished by means of saturated steam at 102° C. for 8 minutes. Then the print is given a warm rinse, subjected to a fastness wash with hot water at 95° C., rinsed warm, and then dried. This gives a blue print having excellent service fastnesses.

What is claimed is:

1. A dye of the formula (I)

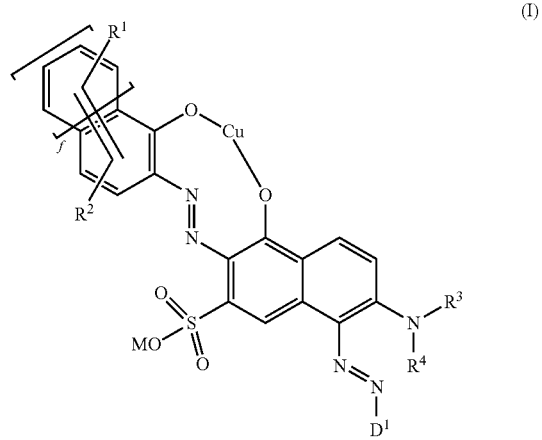

in which
$R^1$ and $R^2$ independently of one another are hydrogen, $(C_1-C_4)$-alkyl, $(C_1-C_4)$-alkoxy, hydroxyl, sulfo, carboxyl, cyano, nitro, amido, or ureido or are a group of the formula $-SO_2-Z^1$, where
$Z^1$ is $-CH=CH_2$, $-CH_2CH_2G$ or hydroxyl, and
G is hydroxyl or an alkali-detachable group;
$R^3$ is $(C_1-C_4)$-alkyl; $(C_1-C_4)$-alkyl substituted by sulfo, carboxyl, halogen, hydroxyl, amino or acetamido; phenyl; or phenyl substituted by $(C_1-C_4)$-alkyl, $(C_1-C_4)$-alkoxy, sulfo, halogen, carboxyl, acetamido or ureido;
$R^4$ is hydrogen or has one of the definitions of $R^3$;
f is 0 or 1;
$D^1$ is a group of the formula (1)

in which
$R^5$ and $R^6$ independently of one another are hydrogen, $(C_1-C_4)$-alkyl, $(C_1-C_4)$-alkoxy, hydroxyl, sulfo, carboxyl, cyano, nitro, amido, ureido or halogen; and
$X^1$ is hydrogen or a group of the formula $-SO_2-Z^2$, where $Z^2$ has one of the definitions of $Z^1$;
$D^1$ is a group of the formula (2)

in which $R^7$ and $R^8$ independently of one another are hydrogen, $(C_1-C_4)$-alkyl, $(C_1-C_4)$-alkoxy, hydroxyl, sulfo, carboxyl, cyano, nitro, amido, ureido or halogen; and $X^2$ has one of the definitions of $X^1$; or $D^1$ is a group of the formula (3)

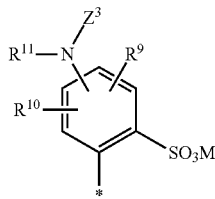

(3)

in which $R^9$ and $R^{10}$ independently of one another have one of the definitions of $R^5$ and $R^6$;

$R^{11}$ is hydrogen, $(C_1-C_4)$-alkyl, or phenyl which is unsubstituted or substituted by $(C_1-C_4)$-alkyl, $(C_1-C_4)$-alkoxy, sulfo, halogen or carboxyl; and $Z^3$ is a group of the formula (4) or (5) or (6)

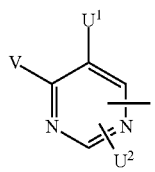

(4)

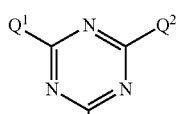

(5)

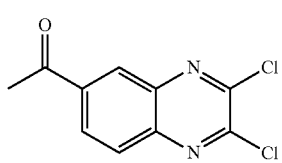

(6)

in which

V is fluorine or chlorine;

$U^1$ and $U^2$ independently of one another are fluorine, chlorine or hydrogen; and $Q^1$ and $Q^2$ independently of one another are chlorine, fluorine, cyanamido, hydroxyl, $(C_1-C_6)$-alkoxy, phenoxy, sulfophenoxy, mercapto, $(C_1-C_4)$-alkylmercapto, pyridino, carboxypyridino or carbamoylpyridino, or are a group of the formula (7) or (8)

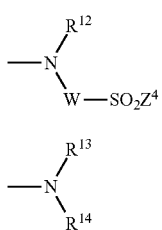

(7)

(8)

in which $R^{12}$ is hydrogen, $(C_1-C_4)$-alkyl, sulfo-$(C_1-C_4)$-alkyl, unsubstituted phenyl or phenyl which is substituted by $(C_1-C_4)$-alkyl, $(C_1-C_4)$-alkoxy, sulfo, halogen, carboxyl, acetamido or ureido;

$R^{13}$ and $R^{14}$ independently of one another have one of the definitions of $R^{12}$ or together form a group of the formula $—(CH_2)_j—$ where j is 4 or 5, or a group of the formula $—(CH_2)_2-E-(CH_2)_2—$, in which E is oxygen, sulfur, sulfonyl or $—N((C_1-C_4)\text{-alkyl})-$;

W is unsubstituted phenylene; phenylene substituted by 1 or 2 substituents selected from the group consisting of $(C_1-C_4)$-alkyl, $(C_1-C_4)$-alkoxy, carboxyl, sulfo, chlorine, and bromine; unsubstituted naphthylene; naphthylene substituted by 1 or 2 sulfo groups; $(C_1-C_4)$-alkylene-arylene; $(C_1-C_4)$-alkylene-arylene which is interrupted by oxygen, sulfur, sulfonyl, $—NH—$, carbonyl, $—CONH—$ or $—CON(CH_3)—$; $(C_2-C_6)$-alkylene; $(C_2-C_6)$-alkylene which is interrupted by oxygen, sulfur, sulfonyl, $—NH—$, carbonyl, $—CONH—$ or $—CON(CH_3)—$; phenylene-CONH-phenylene; or phenylene-CONH-phenylene, where one or both phenylene groups are substituted each by 1 or 2 substituents selected from the group consisting of $(C_1-C_4)$-alkyl, $(C_1-C_4)$-alkoxy, hydroxyl, sulfo, carboxyl, amido, ureido, and halogen; and $Z^4$ has one of the definitions of $Z^1$; or $D^1$ is a group of the formula (9)

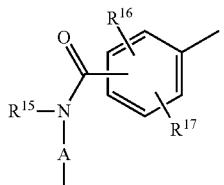

(9)

in which $R^{15}$ is hydrogen, $(C_1-C_4)$-alkyl, aryl or an aryl substituted by one, two or three mutually independent groups from the selected from the group consisting of $(C_1-C_4)$-alkyl, $(C_1-C_4)$-alkoxy, hydroxyl, sulfo, carboxyl, amido, and halogen;

$R^{16}$ and $R^{17}$ independently of one another are hydrogen, $(C_1-C_4)$-alkyl, $(C_1-C_4)$-alkoxy, hydroxyl, sulfo, carboxyl, cyano, nitro, amido, ureido or halogen;

A is a group of the formula (10)

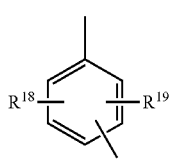

(10)

in which $R^{18}$ and $R^{19}$ independently of one another are hydrogen, $(C_1-C_4)$-alkyl, $(C_1-C_4)$-alkoxy, hydroxyl, sulfo, carboxyl, cyano, nitro, amido, ureido or halogen; or A is a group of the general formula (11)

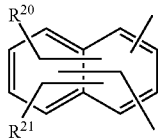

in which
R$^{20}$ and R$^{21}$ independently of one another are hydrogen, (C$_1$-C$_4$)-alkyl, (C$_1$-C$_4$)-alkoxy, hydroxyl, sulfo, carboxyl, cyano, nitro, amido, ureido or halogen; or
A is a group of the formula (12)

$$—(CR^{22}R^{23})_k—\qquad(12)$$

in which
k is an integer greater than 1 and
R$^{22}$ and R$^{23}$ independently of one another are hydrogen, (C$_1$-C$_4$)-alkyl, (C$_1$-C$_4$)-alkoxy, hydroxyl, cyano, amido, halogen or aryl; and
X$^3$ has one of the definitions of X$^1$; and
M is hydrogen, an alkali metal or one equivalent of an alkaline earth metal;
and the dye of the formula (I) comprises at least one fiber-reactive group selected from the group consisting of —SO$_2$—Z$^1$, —SO$_2$—Z$^2$ and Z$^3$.

2. The dye as claimed in claim 1, wherein R$^1$ and R$^2$ independently of one another are hydrogen, methyl, methoxy, sulfo or a group of the formula —SO$_2$—Z$^1$.

3. The dye as claimed in claim 1, wherein R$^3$ is methyl or sulfomethyl and R$^4$ is hydrogen or methyl.

4. The dye as claimed in claim 1, wherein Z$^1$, Z$^2$ and Z$^4$ are vinyl, β-chloroethyl or β-sulfatoethyl.

5. The dye as claimed in claim 2, wherein R$^3$ is methyl or sulfomethyl and R$^4$ is hydrogen or methyl and
Z$^1$, Z$^2$ and Z$^4$ are vinyl, β-chloroethyl or β-sulfatoethyl.

6. The dye as claimed in claim 1, wherein D$^1$ is a group of the formula (1), (3) or (9).

7. The dye as claimed in claim 5, wherein D$^1$ is a group of the formula (1), (3) or (9).

8. The dye as claimed in claim 1, which conforms to the formula (Ib)

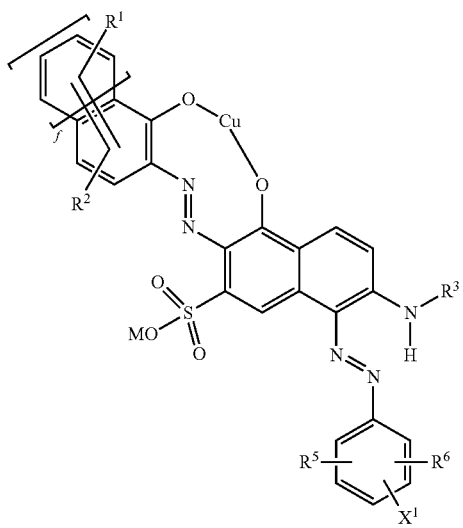

or the formula (Ic)

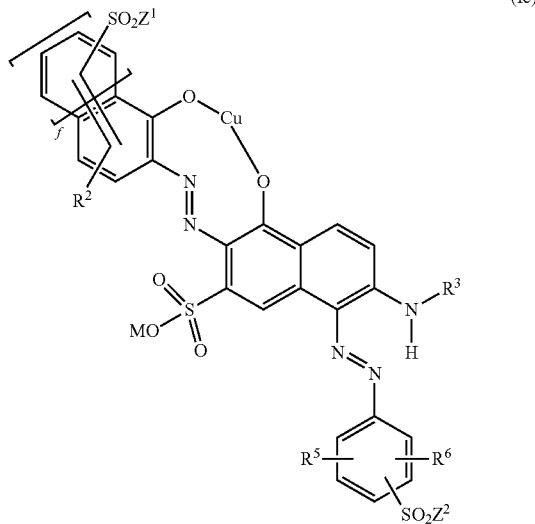

in which R$^1$, R$^2$, R$^3$, R$^5$, R$^6$, X$^1$, Z$^1$, Z$^2$, M, and f are defined as indicated in claim 1.

9. The dye as claimed in claim 1, which conforms to the formula (Ib)

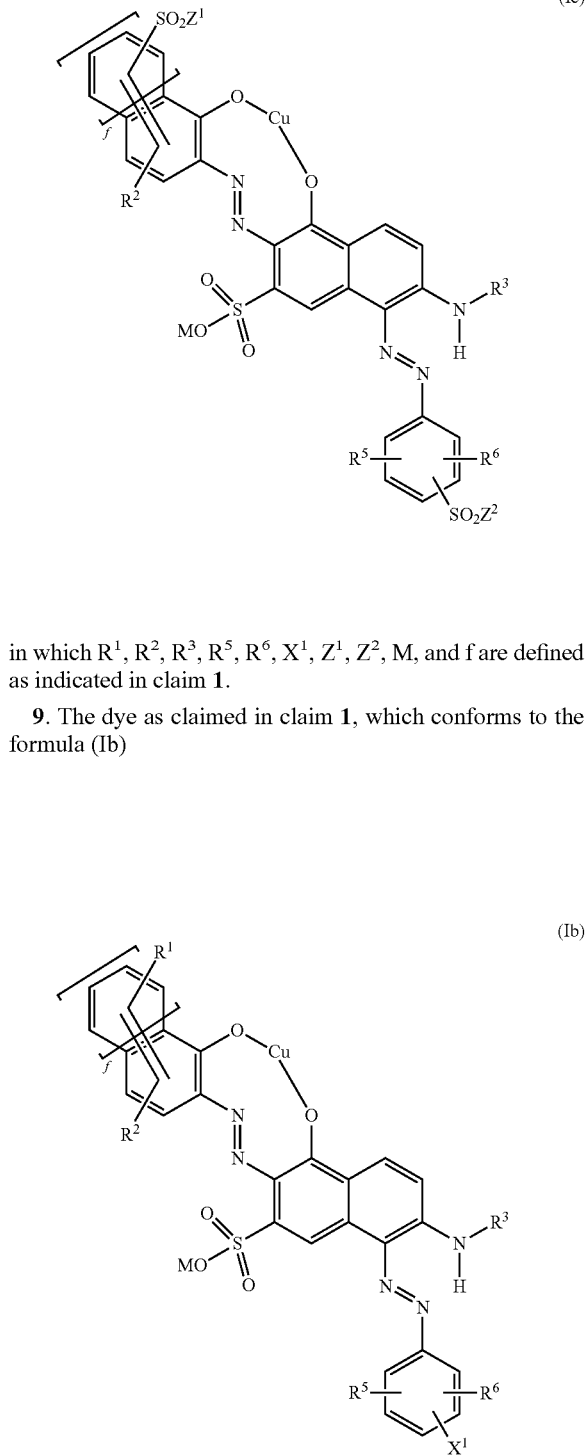

or the formula (Ic)

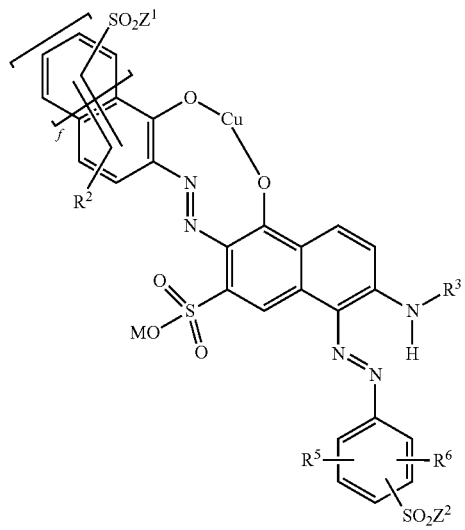

wherein $R^1$ and $R^2$ independently of one another are hydrogen, methyl, methoxy, sulfo or a group of the formula —$SO_2$—$Z^1$, $R^3$ is methyl or sulfomethyl $Z^1$ and $Z^2$ are identical or different and are vinyl, β-chloroethyl or β-sulfatoethyl and $R^5$, $R^6$, $X^1$, M, and f are defined as indicated in claim 1.

10. A process for preparing the dye of the formula (I) as claimed in claim 1, which comprises reacting a compound of the formula (13)

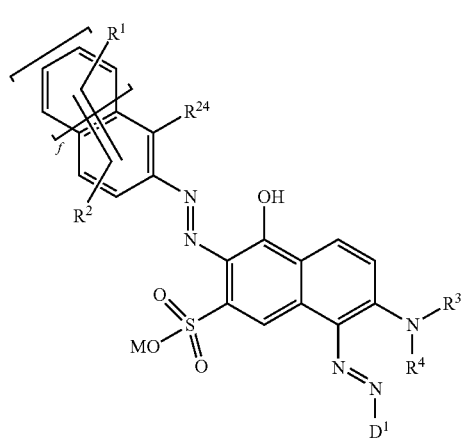

in which $R^{24}$ is hydrogen, hydroxyl or methoxy and $R^1$ to $R^4$, $D^1$, f, and M are defined as indicated in claim 1 with a copper(II) salt.

11. A process for preparing the dye of the formula (I) as claimed in claim 1, which comprises reacting a compound of the formula (18)

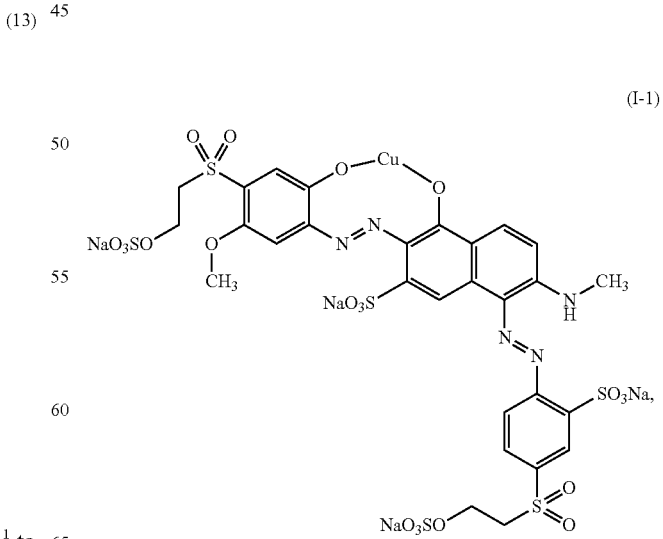

in which $R^1$ to $R^4$, f, and M are defined as indicated in claim 1 with the diazotized compound of an amine of the formula (14)

$$D^1-NH_2 \qquad (14),$$

in which $D^1$ is defined as indicated in claim 1.

12. A process for dyeing or printing carboxamido- and/or hydroxyl-containing material, which comprises contacting the dye of the formula (I) as claimed in claim 1 with the material.

13. An ink for digital textile printing by the inkjet process, which comprises the dye of the formula (I) as claimed in claim 1.

14. A dye of the formula (I-1) through (I-67)

(I-2)
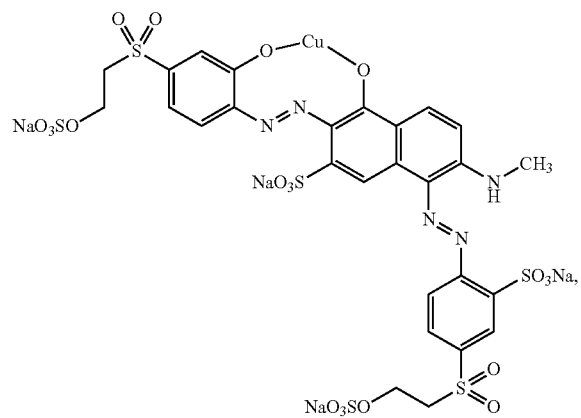
(I-3)
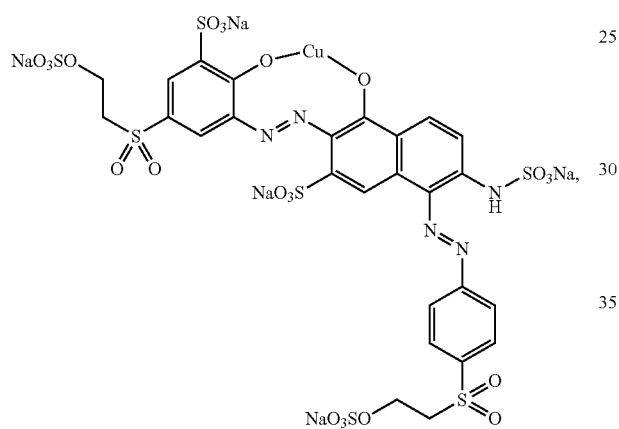
(I-4)
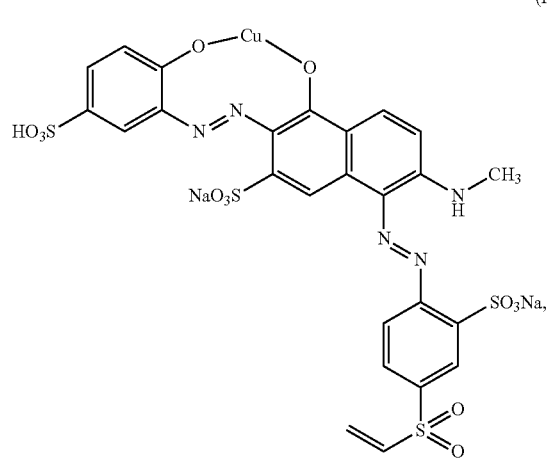
(I-5)
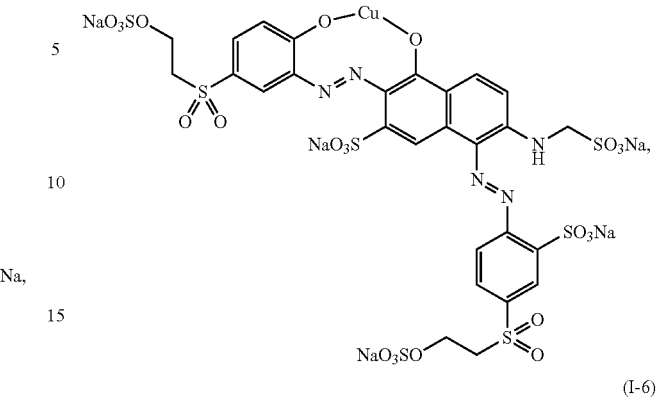
(I-6)
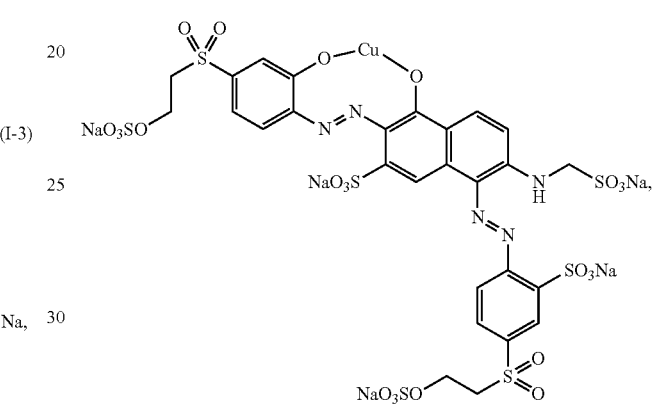
(I-7)
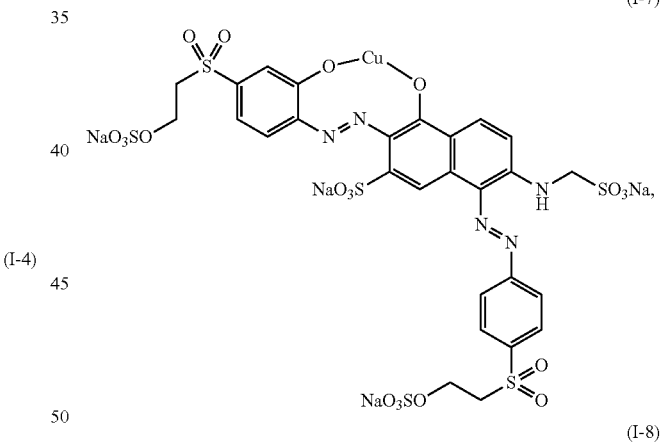
(I-8)
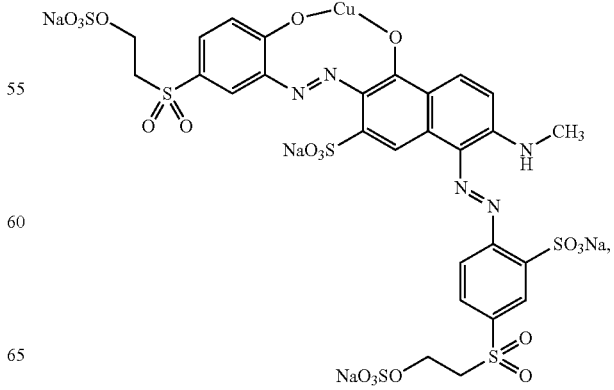

-continued
(I-9)
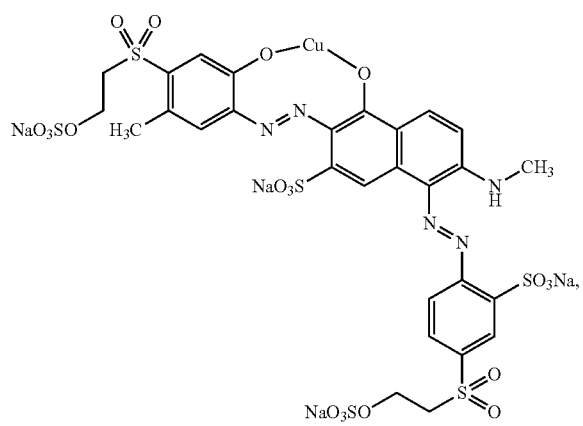
(I-10)
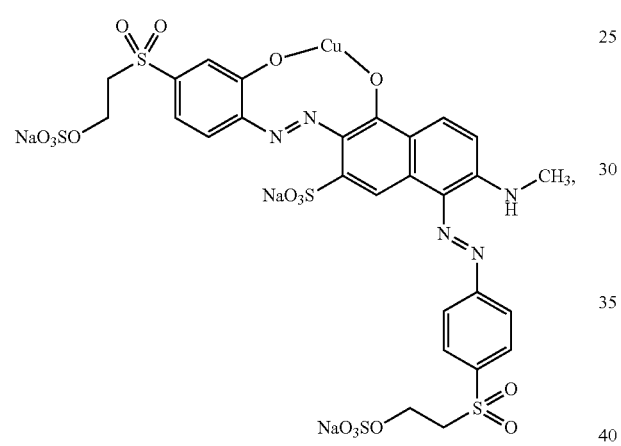
(I-11)
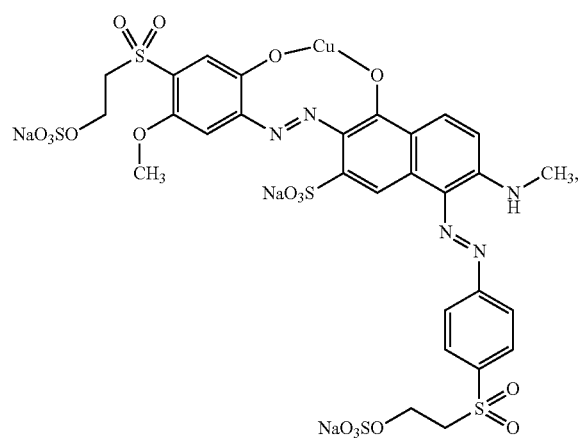
-continued
(I-12)
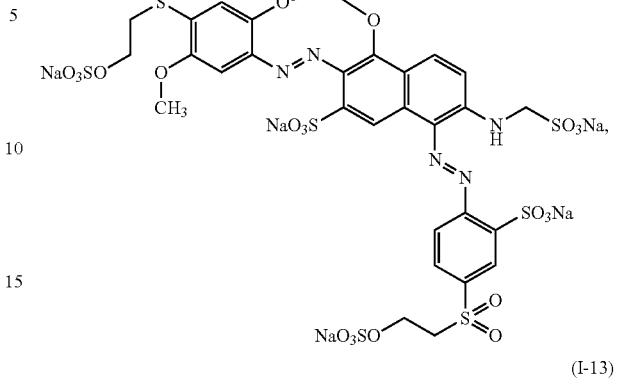
(I-13)
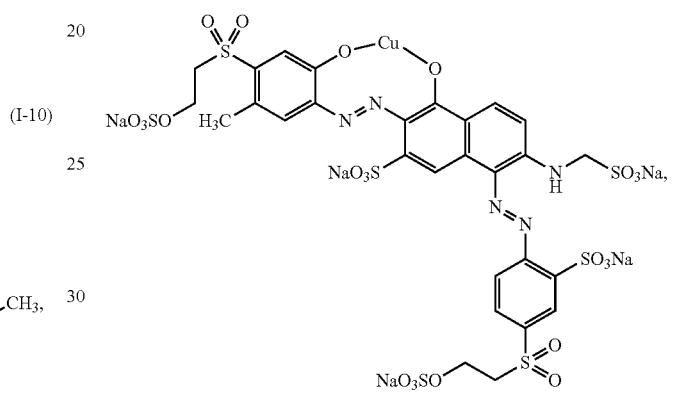
(I-14)
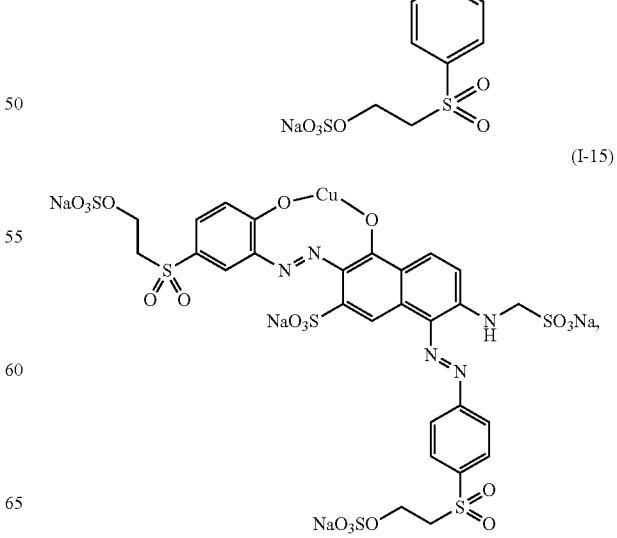
(I-15)
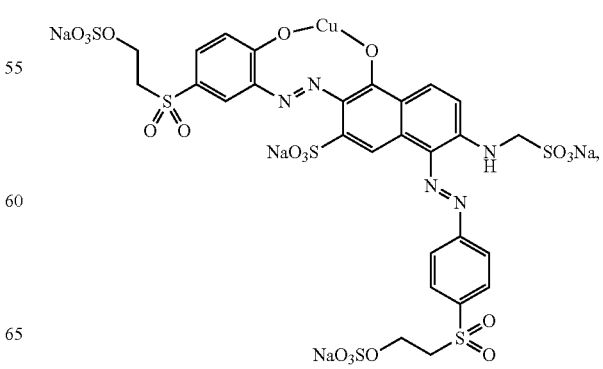

-continued
(I-16)
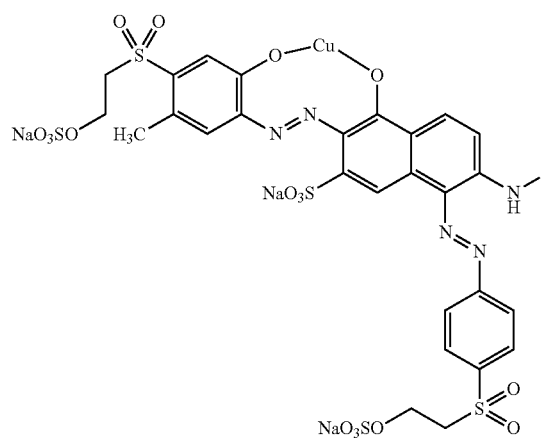
(I-17)
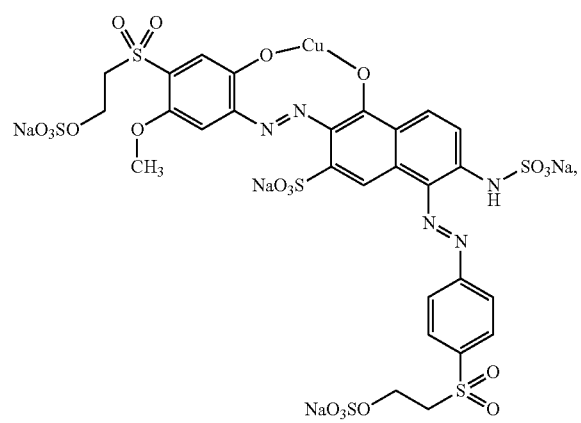
(I-18)
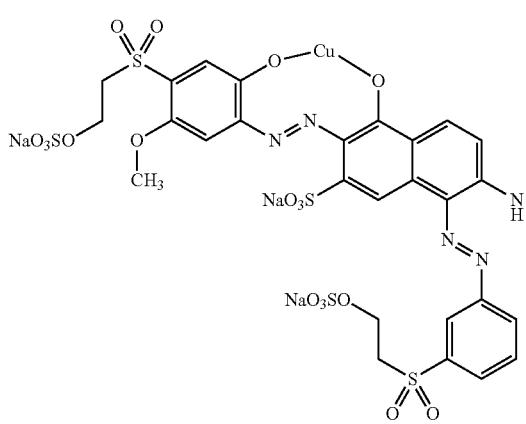
-continued
(I-19)
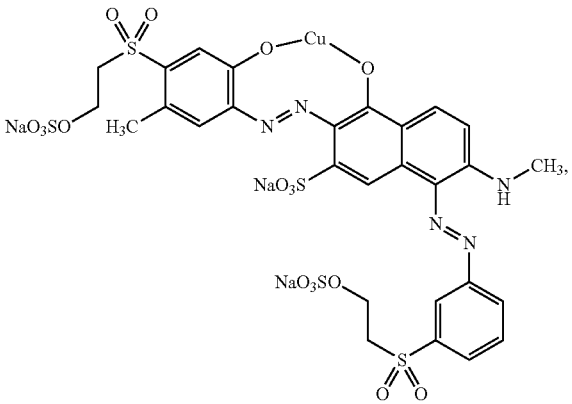
(I-20)
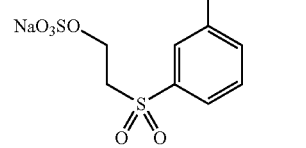
(I-21)
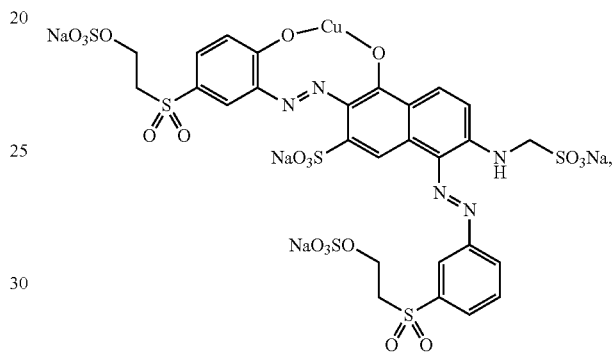
(I-22)
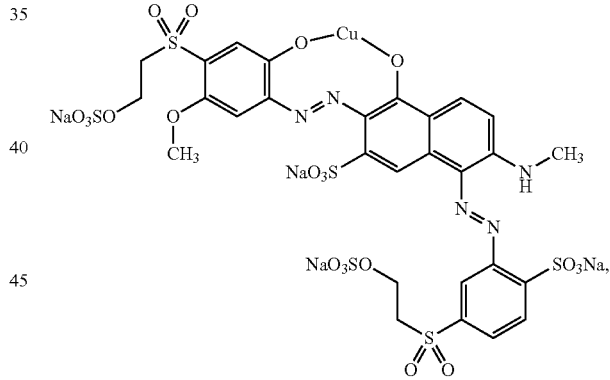

-continued
(I-23)
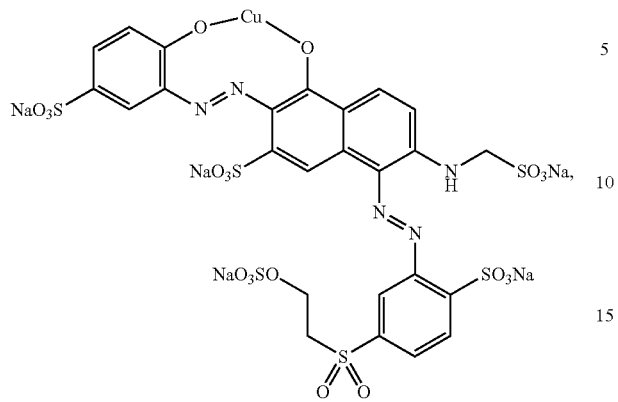
(I-24)
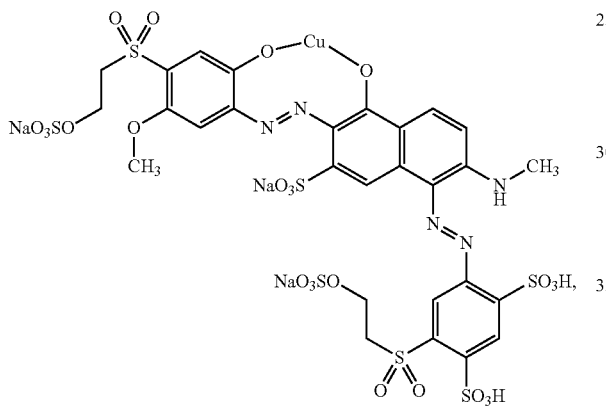
(I-25)
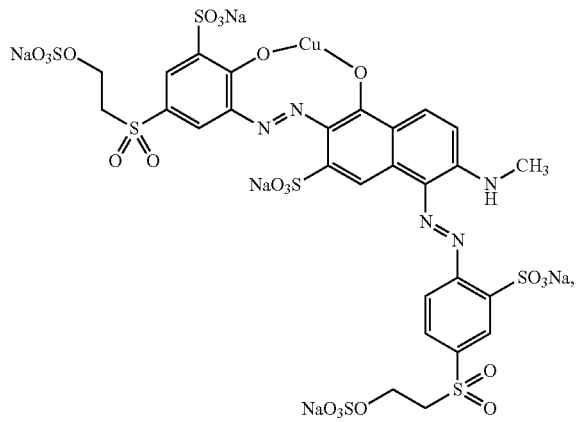
-continued
(I-26)
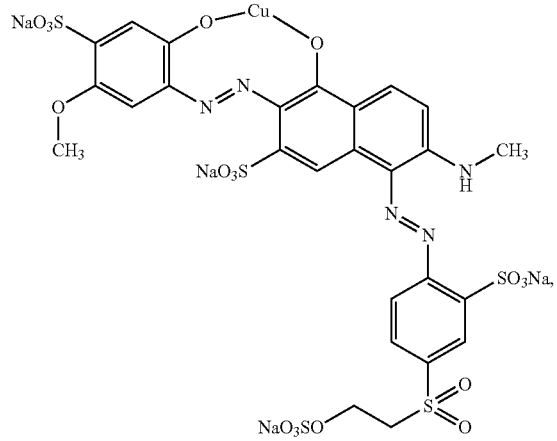
(I-27)
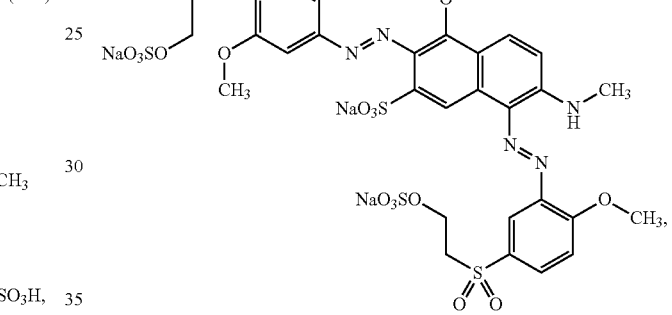
(I-28)
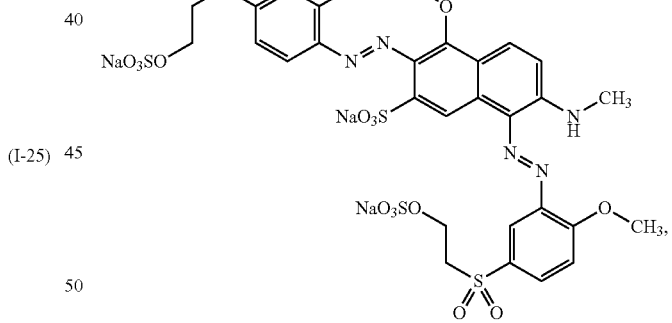
(I-29)
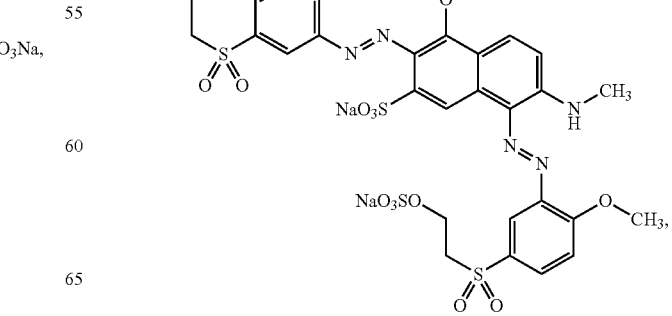

(I-30)
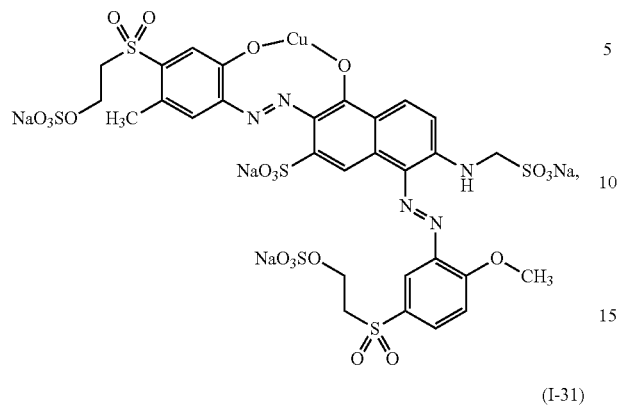
(I-31)
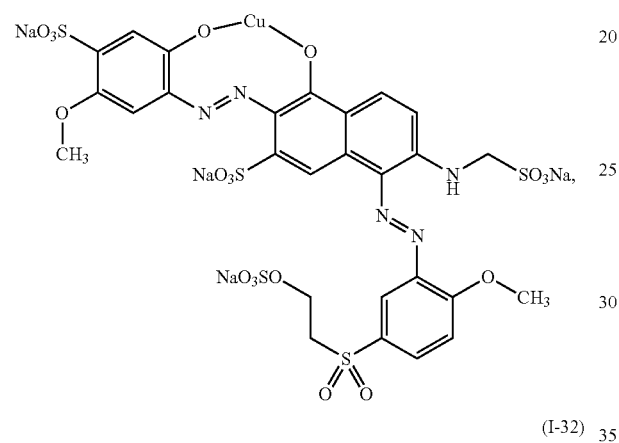
(I-32)
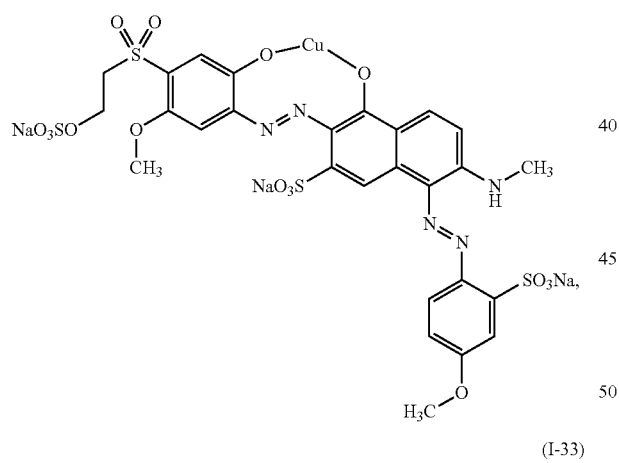
(I-33)
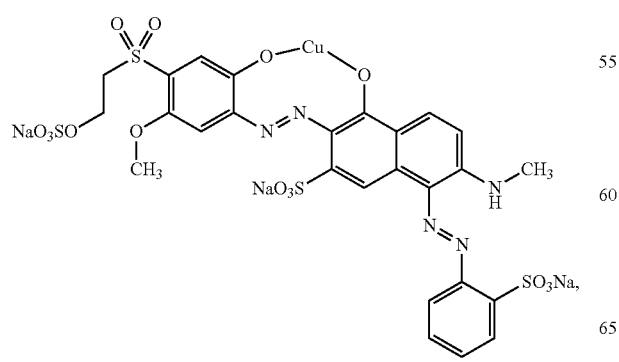
(I-34)
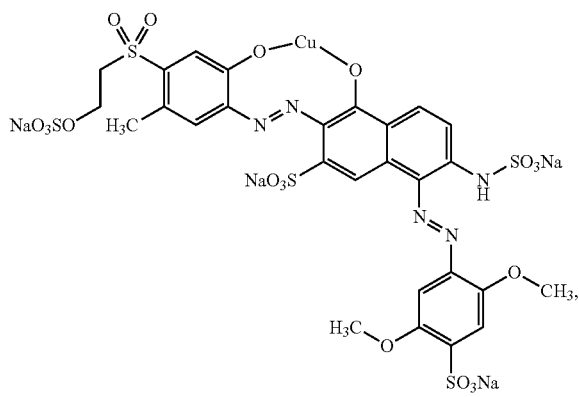
(I-35)
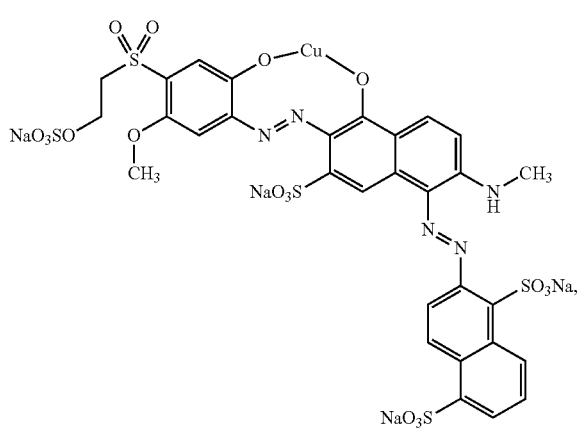
(I-36)
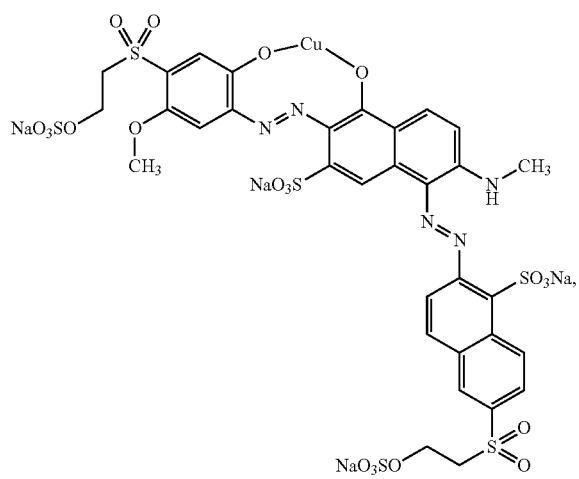

-continued
(I-37)
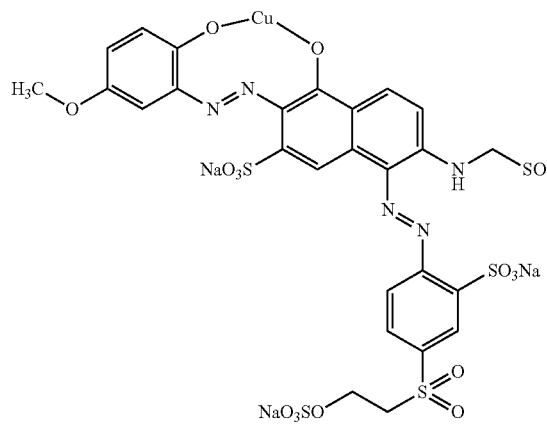
(I-38)
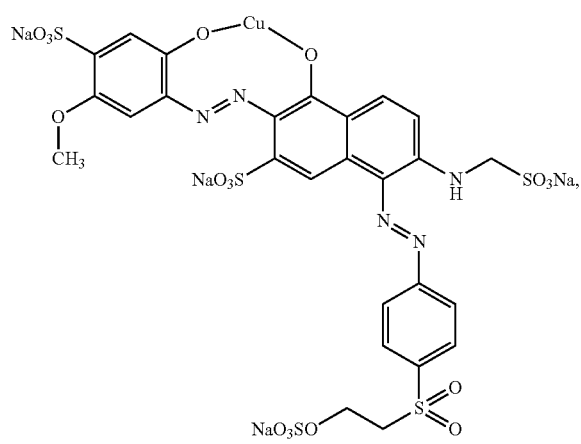
(I-39)
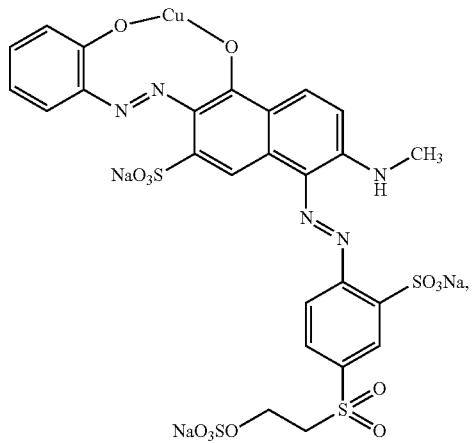
-continued
(I-40)
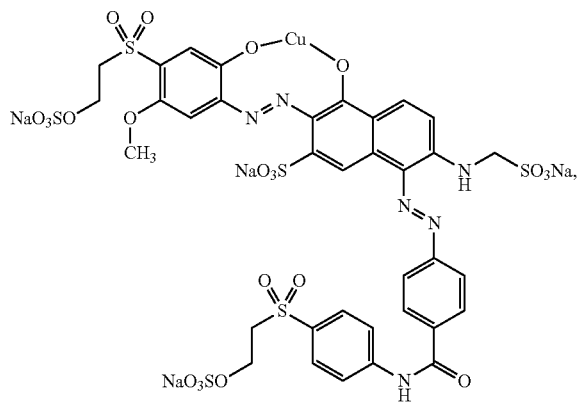
(I-41)
(I-42)
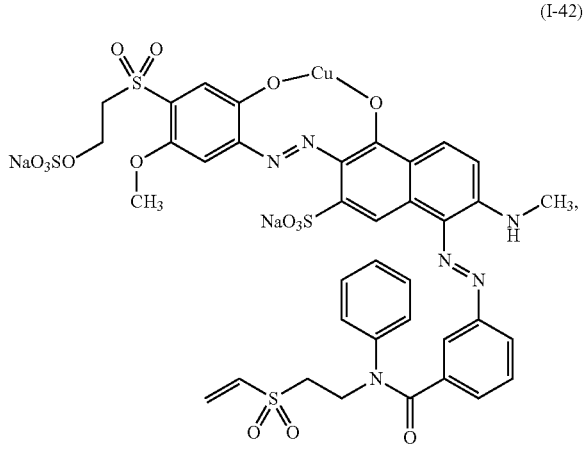

-continued
(I-43)
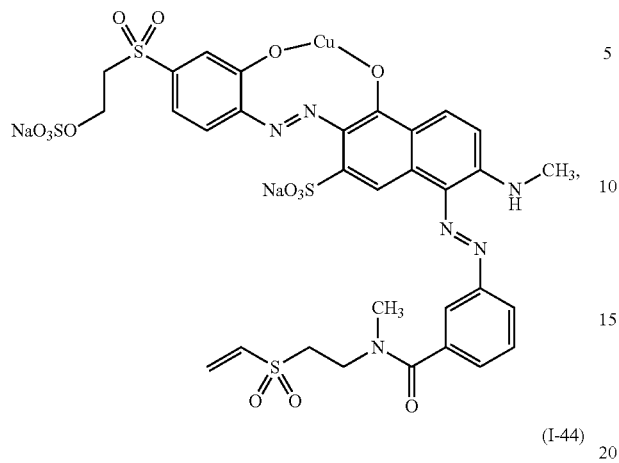
(I-44)
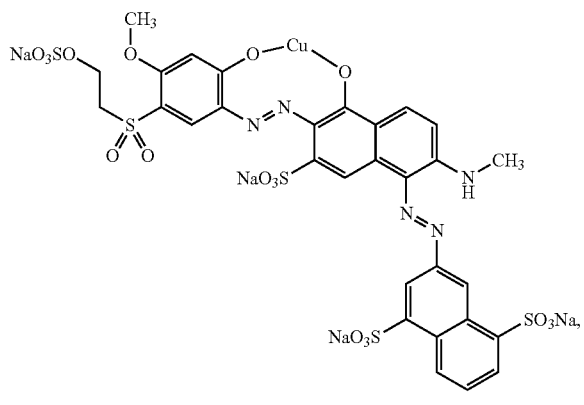
(I-45)
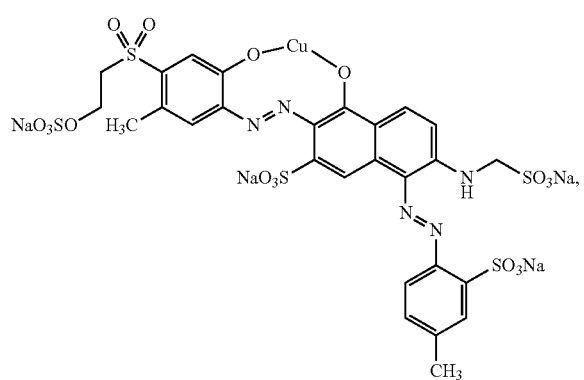
(I-46)
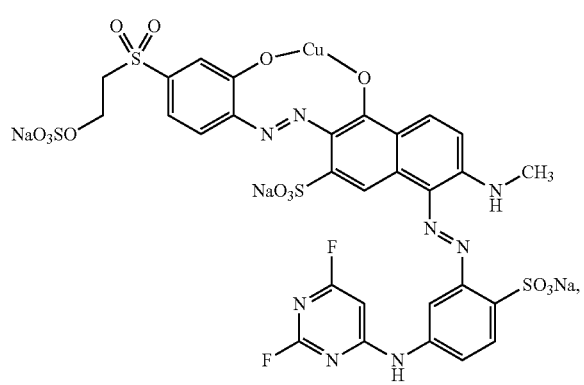
(I-47)
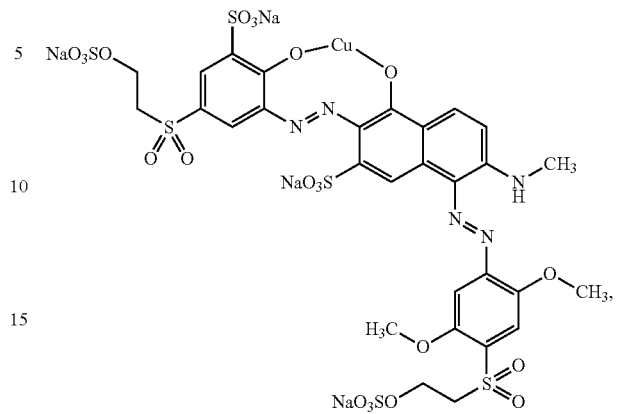
(I-48)
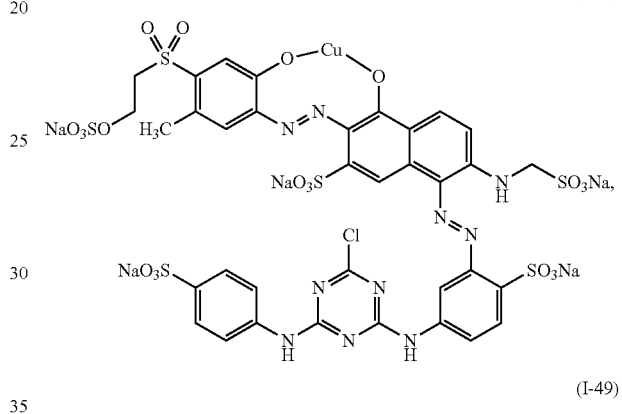
(I-49)
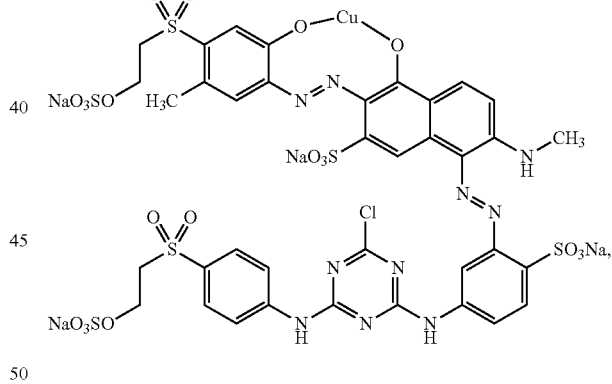
(I-50)
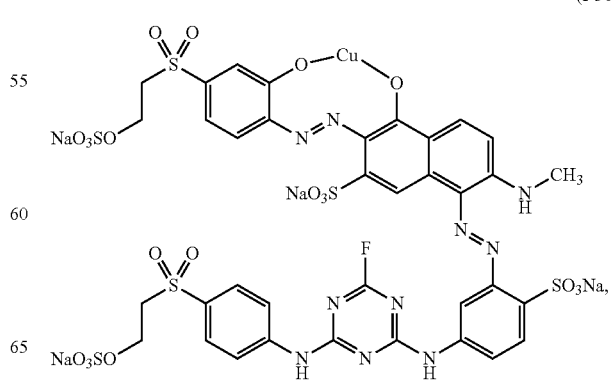

-continued
(I-51)
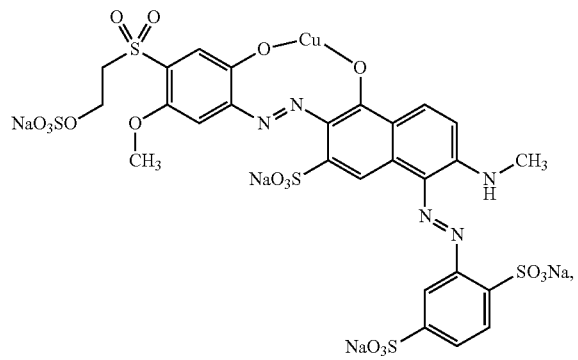
(I-52)
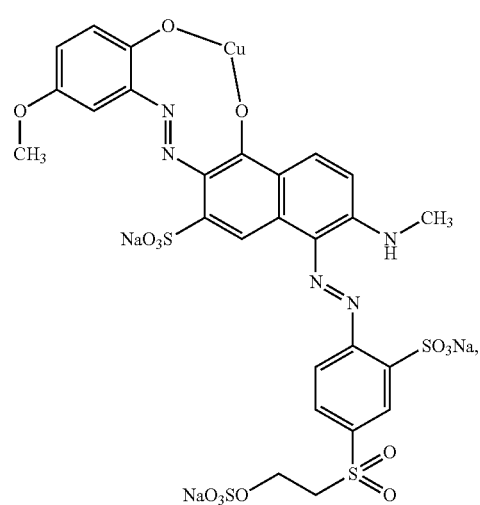
(I-53)
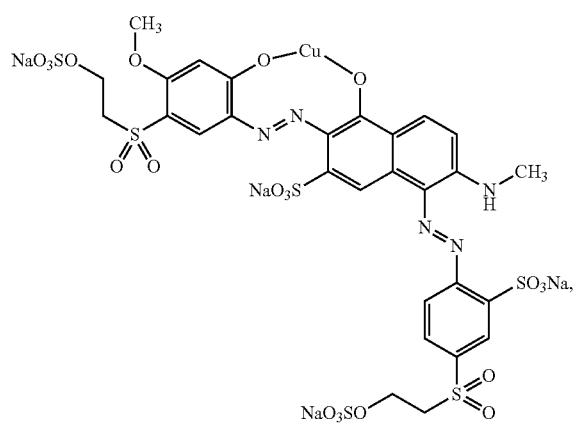
-continued
(I-54)
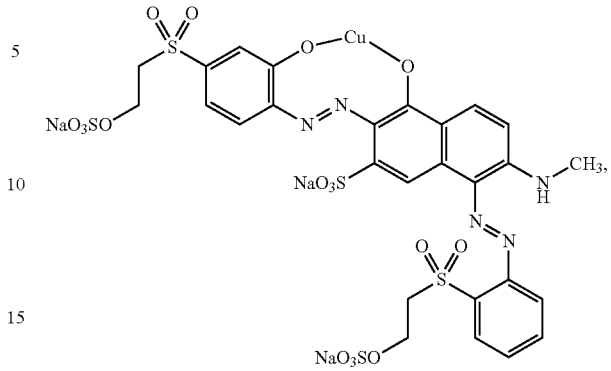
(I-55)
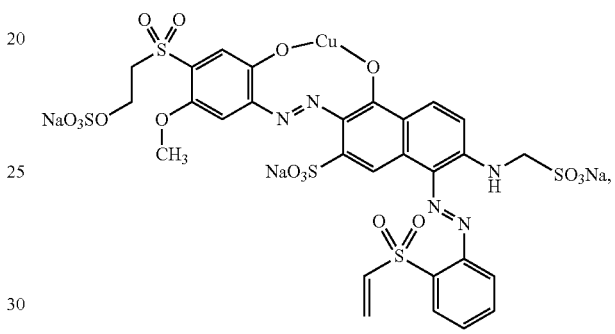
(I-56)
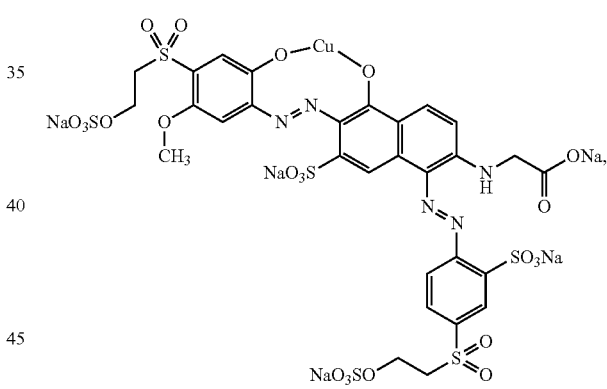
(I-57)
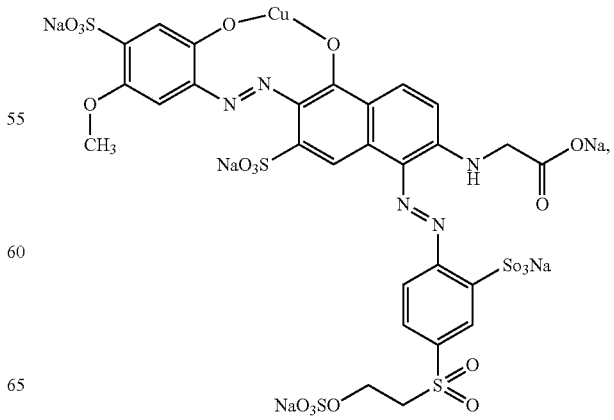

(I-58)
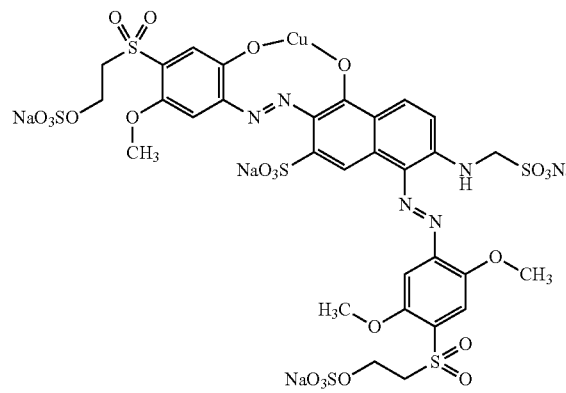
(I-61)
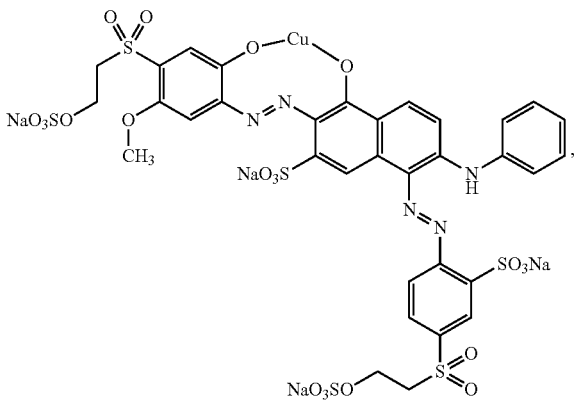
(I-59)
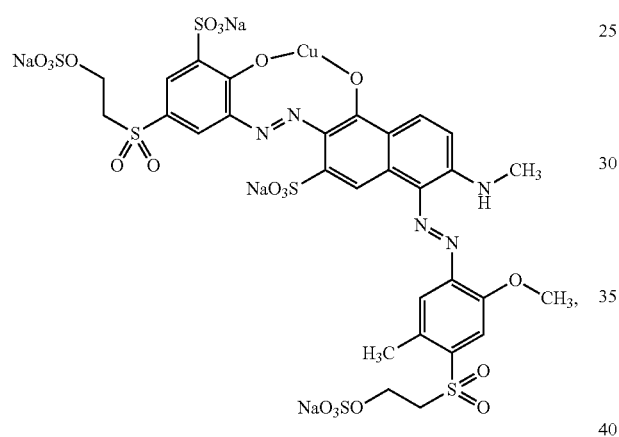
(I-62)
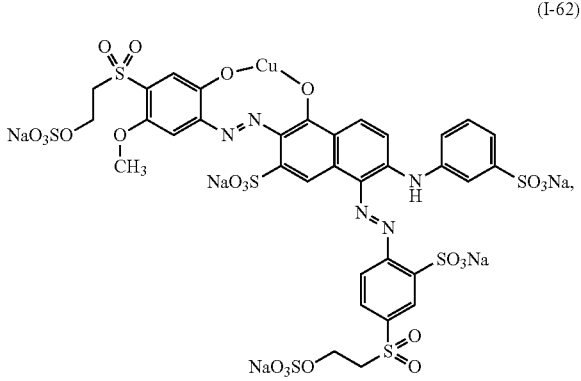
(I-60)
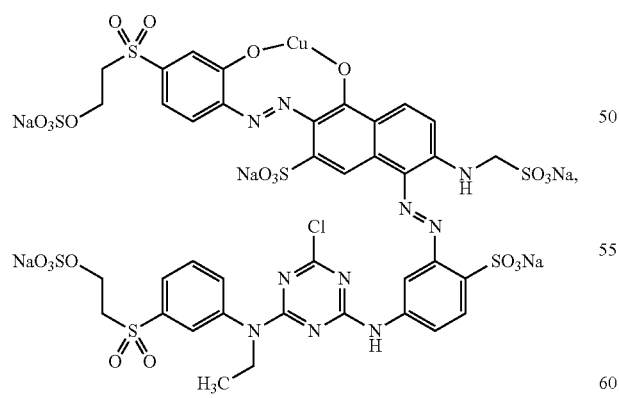
(I-63)
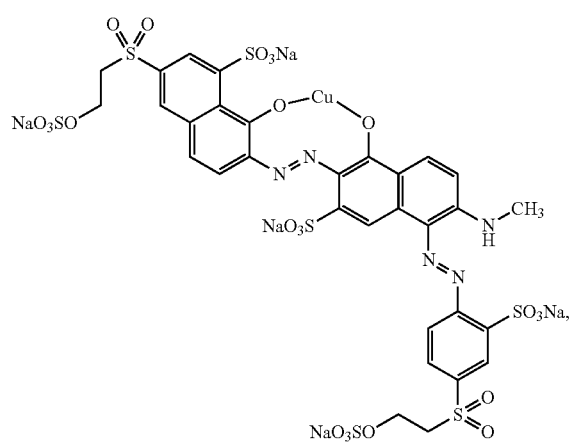

(I-64)
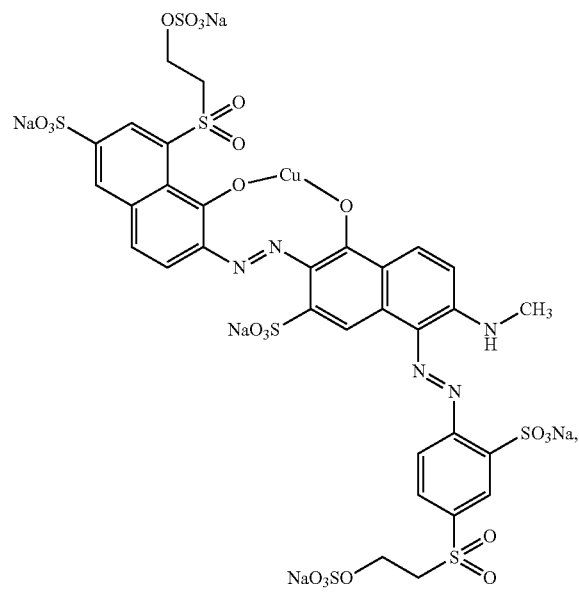
(I-65)
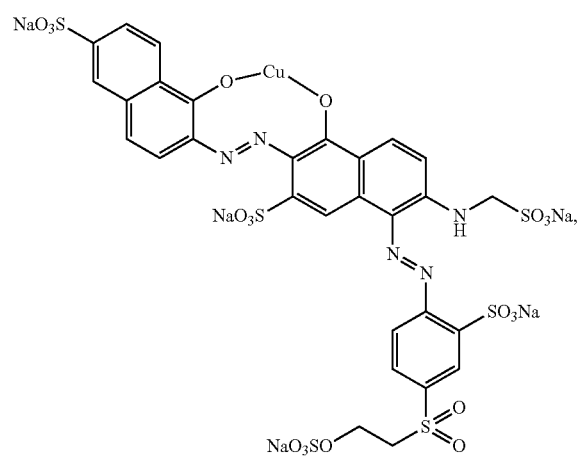
(I-66)
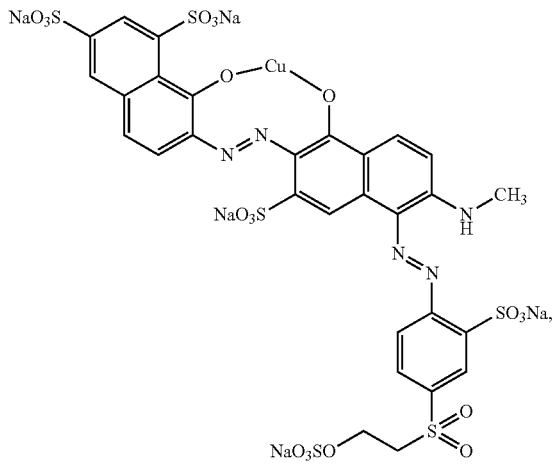
(I-67)
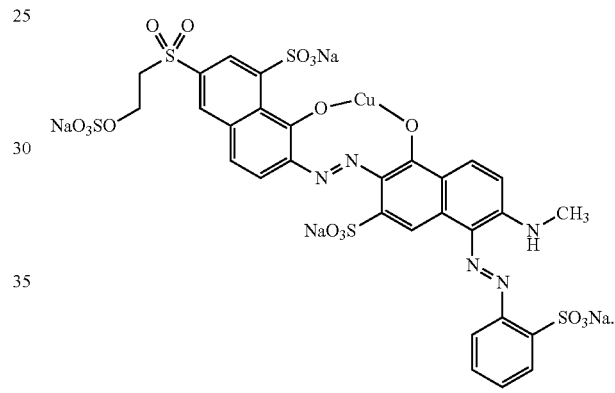
* * * * *